United States Patent [19]
Afonso et al.

[11] Patent Number: 6,130,229
[45] Date of Patent: Oct. 10, 2000

[54] TRICYCLIC COMPOUNDS HAVING ACTIVITY AS RAS-FPT INHIBITORS

[75] Inventors: Adriano Afonso, West Caldwell; Joseph M. Kelly, Parlin; Stuart B. Rosenblum, West Orange; Ronald L. Wolin, Bedminster; Jay Weinstein, Upper Montclair, all of N.J.

[73] Assignee: Schering Corporation, Kenilworth, N.J.

[21] Appl. No.: 08/946,527

[22] Filed: Oct. 7, 1997

Related U.S. Application Data

[60] Provisional application No. 60/028,038, Oct. 9, 1996.

[51] Int. Cl.$^7$ .................... A61K 31/445; C07D 495/04; C07D 491/04
[52] U.S. Cl. .................... 514/291; 514/215; 514/254; 540/577; 544/361; 546/80; 546/89
[58] Field of Search .................. 540/577; 546/80, 546/89; 514/215, 291

[56] References Cited

U.S. PATENT DOCUMENTS

| | | | |
|---|---|---|---|
| 4,826,853 | 5/1989 | Piwinski et al. | 514/290 |
| 5,089,496 | 2/1992 | Piwinski et al. | 514/253 |
| 5,104,876 | 4/1992 | Piwinski et al. | 514/254 |
| 5,151,423 | 9/1992 | Piwinski et al. | 514/254 |
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |
| 5,801,175 | 9/1998 | Afonso et al. | 544/361 |
| 5,852,034 | 12/1998 | Njorge et al. | 514/290 |
| 5,874,442 | 2/1999 | Doll et al. | 514/290 |

FOREIGN PATENT DOCUMENTS

| | | |
|---|---|---|
| 0270818 | 6/1988 | European Pat. Off. . |
| 0396083 | 11/1990 | European Pat. Off. . |
| 0495484 | 7/1992 | European Pat. Off. . |
| WO95/10515 | 4/1995 | WIPO . |
| WO95/10516 | 4/1995 | WIPO . |
| WO95/15949 | 6/1995 | WIPO . |
| WO96/30018 | 10/1996 | WIPO . |
| WO96/30362 | 10/1996 | WIPO . |
| WO96/30363 | 10/1996 | WIPO . |
| WO96/31477 | 10/1996 | WIPO . |
| WO96/31478 | 10/1996 | WIPO . |
| WO97/23478 | 7/1997 | WIPO . |

OTHER PUBLICATIONS

Khosravi–Far et al, *Cell Growth & Differentiation* 3, pp. 461–469 (1992).
Graham, *Exp. Opin. Ther. Patents* 5, pp. 1269–1285 (1995).
Bishop et al., The Journal of Biological Chemistry, vol. 270, No. 15, pp. 30611–306181 (1995).
Njoroge et al., Bioorganic & Medicinal Chemistry Letters, vol. 6, No. 24, pp. 2977–2982 (1996).

*Primary Examiner*—Emily Bernhardt
*Attorney, Agent, or Firm*—Henry C. Jeanette

[57] ABSTRACT

Compounds of Formula I:

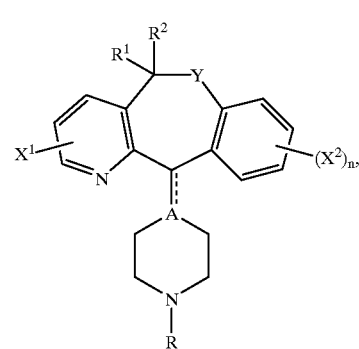

wherein:

$X^1$ is hydrogen, halogen, $CF_3$, nitro, $NH_2$ or lower alkyl;

each $X^2$ is independently selected from the group consisting of hydrogen, halogen, lower alkoxy and lower alkyl;

n is 1 or 2;

Y is selected from the group consisting of $S(O)_p$, O, and $NR^5$, wherein p is 0, 1 or 2, and $R^5$ is hydrogen, alkyl, aryl, cycloalkyl, loweralkoxycarbonyl, aminocarbonyl or acyl;

$R^1$ and $R^2$, which may be the same or different, are selected from the group consisting of hydrogen and lower alkyl groups, or taken together can form an oxygen atom when Y is $NR^5$;

A ... is C=, CH— or N—;

R is —CZ—$Y^1$—$Y^2$—$R^3$, wherein:

Z is O, =CH—CN, or =N—CN;

one of $Y^1$ and $Y^2$ is a bond, —CO—, O, S, or —$NR^4$—, and the other is $(CH_2)_m$, where m is 0 or an integer of 1 to 4, and $R^4$ is H or alkyl, with the proviso that when Z is O and m is 0 then $Y^1$ or $Y^2$ is selected from —CO—, O, S, or —$NR^4$;

$R^3$ is aryl, heteroaryl or heterocycloalkyl, with the proviso that $R^3$ can also be lower alkyl when Z is =N—CN;

and their pharmaceutically acceptable acid addition salts; have activity as Ras-FPT inhibitors. They can be used, e.g., in pharmaceutical compositions, for inhibiting the abnormal growth of cells and for inhibiting proliferative diseases. Processes for their preparation, and useful intermediates, are also disclosed.

11 Claims, No Drawings

TRICYCLIC COMPOUNDS HAVING ACTIVITY AS RAS-FPT INHIBITORS

REFERENCE TO RELATED APPLICATIONS

This application claims the benefit of U.S. Provisional Application Ser. No. 60/028,038 filed Oct. 9, 1996.

FIELD OF THE INVENTION

This invention relates to novel tricyclic compounds having activity as Ras-FPT (farnesyl protein transferase) inhibitors.

BACKGROUND OF THE INVENTION

International Patent Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

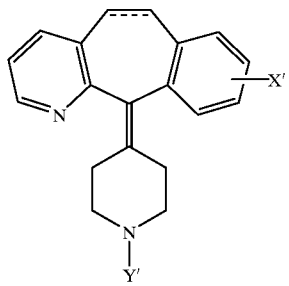

wherein the dotted line represents an optional double bond, X' is hydrogen or halo, and Y' is hydrogen, substituted carboxylate or substituted sulfonyl. For example, Y' can be, amongst others, —COOR' wherein R' is $C_1$ to $C_6$ alkyl or substituted alkyl, phenyl, substituted phenyl, C7 to C12 aralkyl or substituted aralkyl or 2-, 3-, or 4-piperidyl or N-substituted piperidyl. Y' can also be, amongst others, $SO_2R'$ wherein R' is $C_1$ to $C_6$ alkyl, phenyl, substituted phenyl, C7 to Cl 2 aralkyl or substituted aralkyl. Examples of such potentiating agents include 1 1-(4-piperidylidene)-5H-benzo[5,6]cyclohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras p21 oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1934 to 1937, 1993).

In view of the current interest in inhibitors of farnesyl protein transferase, a valuable contribution to the art would be further compounds that can inhibit farnesyl protein transferase. Such a contribution is provided by this invention.

SUMMARY OF THE INVENTION

The present invention provides compounds of Formula I

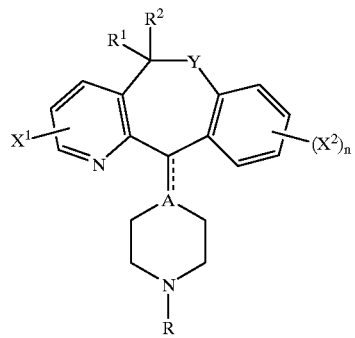

wherein:
$X^1$ is hydrogen, halogen, $CF_3$, nitro, $NH_2$ or lower alkyl;
each $X^2$ is independently selected from the group consisting of hydrogen, halogen, lower alkoxy and lower alkyl;
n is 1 or 2;
Y is selected from the group consisting of S(O)p, O, and $NR^5$, wherein p is 0, 1 or 2, and $R^5$ is hydrogen, alkyl, aryl, cycloalkyl, loweralkoxycarbonyl, aminocarbonyl or acyl;
$R^1$ and $R^2$ are the same or different and are selected from the group consisting of hydrogen and lower alkyl groups, or taken together can form an oxygen atom when Y is $NR^5$;
the dotted line indicates a single or double bond—i.e., the dotted line indicates that the bond from A to C-11 of the tricyclic ring can be a single bond or a double bond;
A is a C atom (when the dotted line indicates a double bond, i.e., when there is a double bond from A to the C-11 of the tricyclic ring) or CH or an N atom (when the dotted line indicates a single bond, i.e., when there is a single bond from A to the C-11 of the tricyclic ring);
R is —CZ—$Y^1$—$Y^2$—$R^3$, wherein:
Z is O, =CH—CN, or =N—CN;
one of $Y^1$ and $Y^2$ is a bond, —CO—, O, S, or —$NR^4$—, and the other is $(CH_2)_m$, where m is 0 or an integer of 1 to 4, and $R^4$ is H or alkyl, with the proviso that when Z is O and m is 0 then $Y^1$ or $Y^2$ is selected from —CO—, O, S, or —$NR^4$;
$R^3$ is aryl, heteroaryl or heterocycloalkyl, with the proviso that $R^3$ can also be lower alkyl when Z is =N—CN;
and their pharmaceutically acceptable acid addition salts.

This invention provides a method for inhibiting FPT (farnesyl protein transferase) using a compound of Formula I defined above which: (i) potently inhibits FPT relative to geranylgeranyl protein transferase I, in vitro; (ii) blocks the phenotypic change induced by a form of transforming Ras which is a farnesyl acceptor but not by a form of transforming Ras engineered to be a geranyl-geranyl acceptor; (iii) blocks intracellular processing of Ras which is a farnesyl acceptor but not of Ras engineered to be a geranylgeranyl acceptor; and (iv) blocks abnormal cell growth in culture induced by transforming Ras.

This invention provides a method for inhibiting the abnormal growth of cells, including transformed cells, by administering an effective amount of a compound of Formula I to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene (e.g., Ras p21); (2) tumor cells in which the Ras protein is activated as a result of oncogenic mutation in another gene; and (3) benign and malignant cells of other proliferative diseases in which aberrant Ras activation occurs. Preferably the cells inhibited are tumor cells expressing an activated ras oncogene, or pancreatic tumor cells, lung cancer tumor cells, myeloid leukemia tumor cells, thyroid follicular tumor cells, myelodysplastic tumor cells, epidermal carcinoma tumor cells, bladder carcinoma tumor cells, colon tumors cells, breast cancer cells and prostate cancer cells. The inhibition of the abnormal growth of cells can occur by the inhibition of Ras farnesyl protein transferase, or by the activation of the Ras protein as a result of oncogenic mutation in genes other than the ras gene.

It is believed that this invention also provides a method for inhibiting proliferative diseases, both benign and malignant, wherein Ras proteins are aberrantly activated as a result of oncogenic mutation in other genes—i.e., the ras gene itself is apparently not activated by mutation to an oncogenic form—with said inhibition being accomplished by the administration of an effective amount of a compound of Formula I described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, lyn, fyn), may be inhibited by the compounds of Formula I described herein.

In another embodiment, the present invention is directed toward a method for inhibiting Ras farnesyl protein transferase and the farnesylation of the oncogene protein Ras by administering an effective amount of a compound of Formula I defined above to mammals, especially humans. The administration of a compound of Formula I to patients, to inhibit farnesyl protein transferase, is useful in the treatment of the cancers described above.

Another aspect of this invention is a pharmaceutical composition for inhibiting the abnormal growth of cells comprising an effective amount of compound of Formula I in combination with a pharmaceutically acceptable carrier.

A further feature of the invention comprises a process for the preparation of a compound of the formula

A1

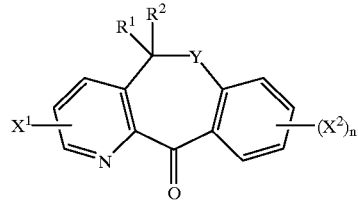

wherein $X^1$, $X^2$, n, $R^1$, $R^2$, and Y are as defined in claim 1, which comprises the step of fusing a compound of the formula

A4

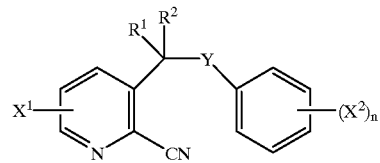

with a Lewis acid catalyst; and contacting the product with an aqueous medium. Compounds of formula A1 are useful intermediates in the preparation of compounds of the Formula I.

DETAILED DESCRIPTION OF THE PREFERRED EMBODIMENTS

Compounds of the Formula I above are selective inhibitors of Ras-FPT and can be used as anti-tumor agents.

In Formula I, when n is 1, $X^2$ is preferably halogen, more preferably Cl (e.g., 10-Cl or 8-Cl), and most preferably 8-Cl.

Compounds of Formula I also include compounds wherein n is 2 and each $X^2$ is the same or differernt halogen. For example, when n is 2 each $X^2$ can be independently selected from Br or Cl. Thus, for example, one $X^2$ can be Cl (e.g., 8-Cl) and the other $X^2$ can be Br (e.g., 7-Br, 9-Br or 10-Br)—e.g., 7-Br and 8-Cl, or 8-Cl and 10-Br.

In another preferred group of compounds, Y is $SO_2$, O, N-alkyl (e.g., N-Me) or S. Preferably, Y is S.

In yet another preferred group of compounds, $R^1$ and $R^2$ are H. Compounds of Formula I also include compounds wherein $R^1$ and $R^2$ are alkyl (e.g., methyl). For example, in compounds wherein $R^1$ and $R^2$ are alkyl Y can be $SO_2$.

A is preferably C (when the dotted line indicates a double bond; i.e., $\overline{A\ldots}$ represents C=) or N (when the dotted line indicates a single bond; i.e., $\overline{A\ldots}$ represents N—).

Preferably, Z is O, $Y^1$ is $CH_2$, $Y^2$ is a bond or S, and $R^3$ is a heteroaryl group, and more preferably $R^3$ is a 3- or 4-pyridinyl group, a 3- or 4-pyridinyl-1-oxide, or a 1-methyl-4-piperidinyl group or a 1-$CONH_2$-4-piperidinyl group (most preferably a 1-$CONH_2$-4-piperidinyl group);

or preferably Z is =N—CN, $Y^1$ is NH, $Y^2$ is $CH_2$, and $R^3$ is a heteroaryl group, and more preferably $R^3$ is a 3- or 4-pyridinyl group or a 3- or 4-pyridinyl N-oxide group.

Particularly preferred compounds of the Formula I above include the following compounds:

4-(3-Bromo-8-chloro-5,11-dihydro[1]benzoxepino-[4,3-b]pyridin-11-ylidene)-1-(4-pyridine-piperidine N1-oxide having the formula

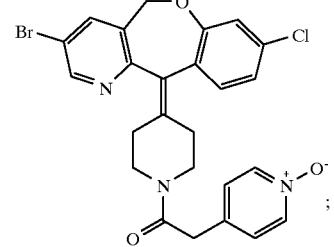

;

| | |
|---|---|
| 4-(8-Chloro-5,11-dihydro[1]benzothiepino-[4,3-b]pyridin-11-yl)-N-cyano-N'-(4-pyridinyl-methyl)-1-piperazine-carboximidamide having the formula | 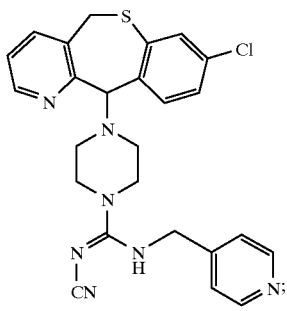 |
| 4-(8-Chloro-5,11-dihydro[1]benzothiepino-[4,3-b]pyridin-11-ylidene)-N-cyano-N'-(4-pyridinyl-methyl)-1-piperidine-carboximidamide having the formula | 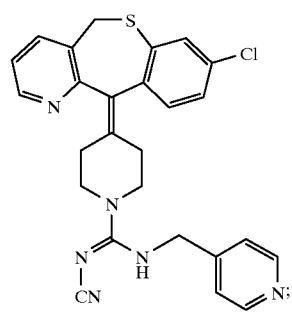 |
| 4-(8-Chloro-5,11-dihydro[1]benzothiepino-[4,3-b]pyridin-11-ylidene)-N-cyano-N'-(3-pyridinyl-methyl)-1-piperidine-carboximidamide N1-oxide having the formula | 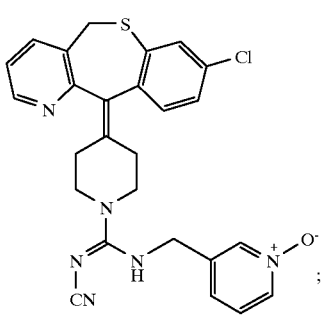 |
| 4-(8-Chloro-5,11-dihydro[1]benzothiepino-[4,3-b]pyridin-11-yl)-N-cyano-N'-(3-pyridinyl-methyl)-1-piperazine-carboximidamide N1-oxide having the formula | 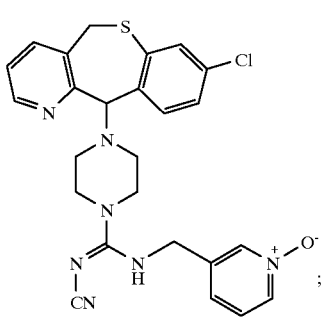 |
| 4-(8-Chloro-5,11-dihydro[1]benzothiepino-[4,3-b]pyridin-11-yli-dene)-1-(pyridine-4-acetyl)-piperidine having the formula | 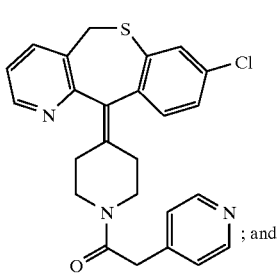 ; and |
| 4-(8-Chloro-6,11-dihydro-6-methyl-5H-pyrido[3,2-c][1]-benzazepin-11-yl)-N-cyano-N'-(4-pyridinylmethyl)-1-piperazine-carboximidamide having the formula | 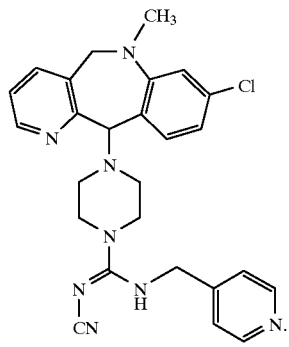 . |

Except where stated otherwise the following definitions apply throughout the present specification and claims. These definitions apply whether a term is used by itself or in combination with other terms. For example, the definition of "alkyl" applies to "alkyl" as well as the "alkyl" portions of "alkoxy", "haloalkyl", "alkylidenedioxy", etc.

Alkyl represents a straight or branched saturated hydrocarbon chain having 1 to 6 carbon atoms, preferably a lower alkyl group having 1 to 4 carbon atoms and especially a methyl or ethyl group.

Cycloalkyl represents a saturated carbocyclic ring having 3 to 7 carbon atoms, e.g., cyclopentyl or cyclohexyl.

Heterocycloalkyl represents a saturated ring having 3 to 6 carbon atoms and in addition one or two atoms selected from O, N and S, and optionally substituted on C and/or on N by lower alkyl, and on N by acyl, alkoxycarbonyl (especially t-butyloxycarbonyl), and aminocarbonyl. Preferred heterocycloalkyl groups include piperidinyl, especially 4-piperidinyl, 1-(1,1-dimethylethoxycarbonyl)piperidinyl, especially 1-(1,1-dimethylethoxycarbonyl)piperidin-4-yl, 1-methylpiperidinyl, especially 1-methylpiperidin-4-yl, and 1-aminocarbonyl-piperidinyl, especially 1-aminocarbonylpiperidin-4-yl.

Acyl represents a group $R^6CO-$ of a carboxylic acid generally represented by $R^6COOH$, and thus includes groups of the formula Alkyl—CO—, Aryl—CO—, Aralkyl—CO—, and Cycloalkyl—CO—, wherein the various groups Alkyl, Aryl, Aralkyl and Cycloalkyl are as defined in this section.

Aryl represents phenyl, naphthyl or indanyl, each of which may be substituted with one to three groups Ra wherein each group $R^a$ is selected from the group consisting of halo, alkyl, polyhaloalkyl (especially $CF_3$), hydroxy, alkoxy, nitro, phenoxy, amino, acylamino, alkylamino, N-alkyl-N-acylamino, and dialkylamino groups, or two groups $R^a$ on adjacent carbon atoms can represent an alkylidenedioxy group. Preferred aryl groups are phenyl, phenyl substituted with fluorine, chlorine, nitro, methyl or methylenedioxy, 1-naphthyl, 2-naphthyl and indanyl groups.

Heteroaryl represents a cyclic group having at least one O, S and/or N interrupting a carbocyclic ring structure and having a sufficient number of delocalized pi electrons to provide aromatic character, with the aromatic heterocyclic group having from 2 to 9, preferably from 4 to 9, carbon atoms, e.g., 2-, 3- or 4-pyridinyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-(1,2,4-triazinyl), 3- or 5-(1,2,4-thiadiazolyl), 2-, 3-, 4-, 5-, 6- or 7-benzofuranyl, 2-, 3-, 4-, 5-, 6- or 7-indolyl, 3-, 4- or 5-pyrazolyl, or 2-, 4- or 5-oxazolyl, etc. Preferred heteroaryl groups are 2-, 3- or especially 4-pyridinyl, 2- or 3-furyl, 2- or 3-thienyl, 2-, 4- or 5-imidazolyl or 7-indolyl. Hetero-aryl groups also include N-oxides of those nitrogen-containing heterocycles that readily form N-oxides, e.g., N-oxides of 2-, 3- and especially 4-pyridinyl groups.

Halogen indicates fluorine, chlorine, bromine or iodine.

Polyhalo indicates substitution by at least 2 halo atoms (e.g., 2, 3, or 4) in the group modified by the term "polyhalo" (and preferably represents trifluoromethyl).

Each group that appears more than once in a structural formula, for example $X^2$, may be independently selected from the whole definition for that group.

A particular compound of Formula I may exist in more than one stereoisomeric configuration, depending for example on the nature of the groups $R^1$ and $R^2$. Further stereoisomerism may be present when X is SO, and within Formula I there are still further possibilities for stereoisomerism, e.g., at the 11-position when the dotted line indicates a single bond. Geometrical isomerism is possible for those compounds of the Formula I wherein Z is =CH—CN. All possible isomers, especially stereoisomers, of Formula I are within the scope of the invention, as are their mixtures, including racemic mixtures.

The tricyclic compounds of Formula I are basic and form acid addition salts, e.g. with pharmaceutically acceptable salts. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia or sodium bicarbonate. The free base forms differ from their respective salt forms somewhat in certain physical properties, such as solubility in polar solvents, but the acid and base salts are otherwise equivalent to their respective free base forms for purposes of the invention. All such salts are considered equivalent to the corresponding free bases for purposes of the invention.

Compounds of the Formula I can be prepared in general by methods that are known in the art. Such methods are described in the following Schemes A–G, wherein $R^b$ is the group R, H or (generally and most preferably) a nitrogen-protecting group such as a lower alkyl group, especially methyl. After the reaction shown in Scheme A, B or C, it may be necessary to carry out a finishing step given in Scheme D, E, F and/or G to obtain a compound of the Formula I. For example, when $R^b$ in a Scheme below is the group H or a nitrogen-protecting group, the conversion of $R^b$ into the group R can be carried out as shown in Scheme G. Moreover, groups such as —NH— in Y (when $R^5$ is H) and $NH_2$ in $X^1$ may need protecting for at least one of the steps to which they will be subjected in these schemes; such protection is standard in the art. A group —NH—or $NH_2$ can be protected with (for example) a benzyloxycarbonyl group or a t-butyloxycarbonyl group (which can later be removed by hydrogenation or acid hydrolysis, respectively). Except for such protection, the various groups, the dotted line and n in the formulae in the Schemes are as defined for Formula I, unless otherwise stated.

SCHEME A:

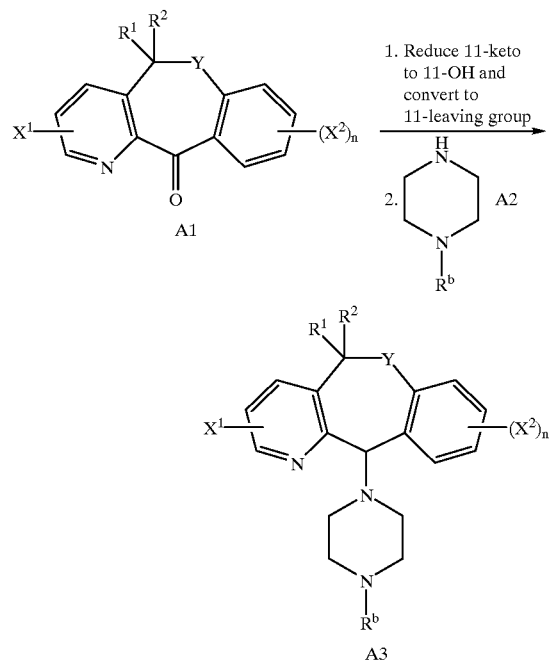

In Scheme A, the tricyclic nucleus is already provided by the compound of formula A1, and the piperazine 'tail' is added on. Replacement of the 11-keto group of the compound of the formula A1 by a leaving group can be effected by reduction and transformation of the resulting hydroxy group into an activated leaving group, especially a mesylate or tosylate, or a halide. Reduction can be effected by means of a borohydride, e.g., $NaBH_4$, in an organic or aqueous organic solvent. Transformation into the mesylate or tosylate can be effected with the appropriate sulfonyl chloride and a tertiary amine base; transformation into the halide can be effected with a halogenating agent such as thionyl chloride or bromide in an inert organic solvent such as methylene chloride. The condensation of the resulting mesylate, tosylate or halide with the compound of the formula A2 is preferably carried out in an organic solvent in the presence of a base serving as acid-binding agent; an excess of a liquid base (e.g., a tertiary amine such a pyridine or triethylamine) can serve as solvent.

In the preparation of the compound of the formula A1 by fusing a compound of the formula A4

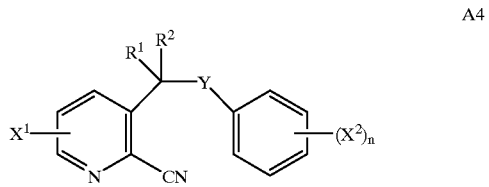

with a Lewis acid catalyst, and then contacting the product with an aqueous medium, the Lewis acid is preferably $AlCl_3$. The product (probably the imine corresponding to the compound of formula Al, or a complex thereof with $AlCl_3$) is converted into the tricyclic ketone of the formula A1 by contact with water during work-up.

SCHEME B:

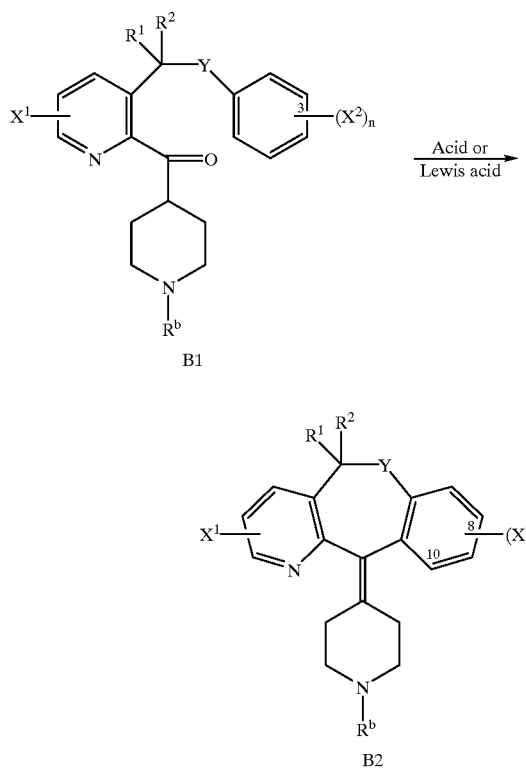

In Scheme B, the piperidine 'tail' is already present in the compound of formula B1, and the tricyclic nucleus is assembled. In this reaction, the acid is preferably concentrated sulfuric acid or polyphosphoric acid; the Lewis acid is preferably boron trifluoride, titanium tetrachloride, aluminum chloride or other Friedel-Crafts catalyst. When boron trifluoride, titanium tetrachloride, or aluminum chloride is used as Lewis acid, the reaction can be effected in the presence of an anhydrous organic solvent; however, it is frequently preferred to fuse the reactant of the formula B1 with aluminum chloride or heat it neat with titanium tetrachloride. The acid or Lewis acid chosen can determine the nature of the product; for example, a 3-chlorophenyl compound of the formula B1 will give predominantly an 8-chloro compound of the formula B2 and comparatively little 10-chloro compound when aluminum chloride is used as catalyst, but a much larger proportion of 10-chloro compound of the formula B2 when titanium tetrachloride is used as catalyst.

When the benzene ring in the compound of the formula B1 is asymmetrically substituted by the group or groups $X^2$, then the resulting compound of Formula I may be a mixture of products. Such a mixture can be separated into its constituents by standard methods such as recrystallization or chromatography.

SCHEME C:

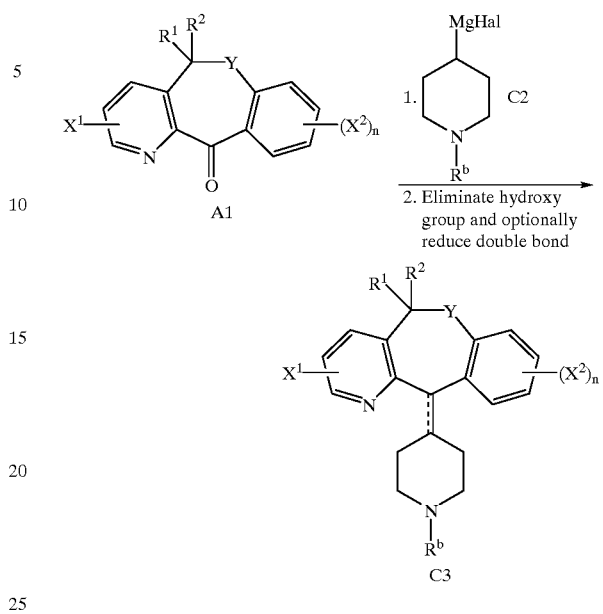

In Scheme C, the tricyclic nucleus is already provided by the compound of formula A1, and the piperidine 'tail' is added on. The Grignard reaction of the compounds of the formulae C1 and C2 can be carried out in an inert anhydrous organic solvent, preferably an ether such as diethyl ether, dioxane or THF. The elimination of the hydroxy group can be effected with a dehydrating agent such as concentrated sulfuric acid, polyphosphoric acid, or acetyl chloride with glacial acetic acid and acetic anhydride, or with 'Burgess reagent' (methoxycarbonyl-sulfamoyltriethylammonium hydroxide) in an inert organic solvent such as an aromatic hydrocarbon, e.g., benzene. Optional reduction of the exocyclic 11-double bond can be effected with hydrogen and a catalyst, e.g., Pt, Pd or Raney nickel, or with Dibal-H.

After Scheme A, B or C has been carried out, a number of finishing steps may be necessary to provide a desired compound of Formula I, in particular by substituting the tricyclic nucleus or by replacing the group $R^b$ by R; such finishing steps are shown in the following Schemes D, ,E, F and G:

SCHEME D:

A 6-thia compound of the Formula I, i.e., a compound wherein Y is S, can be oxidized to a compound wherein Y is SO or $SO_2$. Moreover, a 6-thia-6-oxide (or sulfoxide) of the Formula I, i.e., a compound wherein Y is S=O, can be oxidized to a compound wherein Y is $SP_2$ (or sulfone). This is shown in the following Scheme, wherein $R^b$ is the group R, H or a nitrogen-protecting group, $Y^3$ in the compound of the formula D1 is S or SO, and $Y^4$ in the compound of the formula D2 is SO (except when $Y^2$ is SO) or $SO_2$:

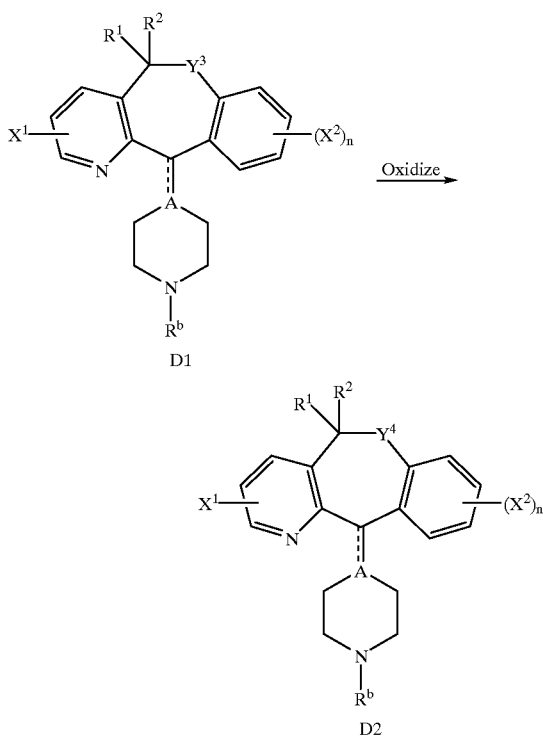

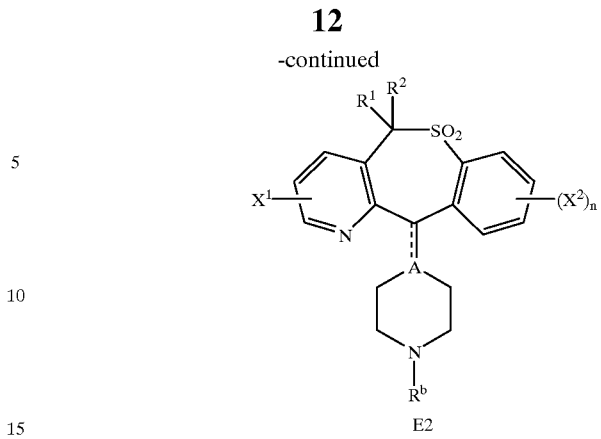

The reaction can be controlled to allow the introduction of only one group $R^1$ or $R^2$ if desired. In general, however, it is much preferred to carry out this reaction at an earlier stage of the synthesis, e.g., on a ketone of formula C1 (see Scheme C) wherein $R^1$ and $R^2$ are both H and Y is $SO_2$.

SCHEME F:

A further substituent, especially a halogen atom, can be introduced into the fused pyridine or benzene ring when Y is $NR^5$ or especially O. Thus, reaction of a compound of Formula I lacking a substituent at the 9-position with DBH in sulfuric acid typically introduces a 9-bromine atom.

A nitro or $NH_2$ group or a halogen atom (especially bromine) can be introduced into the fused pyridine ring of a compound of Formula I. Thus, reaction of a compound of Formula I lacking a substituent at the 3-position with a tetraalkylammonium nitrate (preferably tetrabutylammonium nitrate) in trifluoroacetic anhydride (TFA, preferably in the presence of an inert organic solvent such as methylene chloride) at moderately low temperature, e.g., about 0° C., yields the 3-nitro compound. This process works particularly well in the 6-oxa series. The nitro group can then be replaced with other groups by standard methods; for example, with amino by reduction (e.g., with $Fe/CaCl_2$ in EtOH/water) and then if desired with bromine by diazotization and bromination. This process is illustrated for a compound of the invention in the following scheme, but is not restricted to this embodiment:

The oxidizing agent is preferably a peracid such as peracetic acid, 3-chloroperbenzoic acid, or perboric acid, but can also be DBH (1,3-dibromo-5,5-dimethyl-hydantoin) in acetic acid or $NaNO_3$ in $H_2SO_4$ for the preparation of the sulfoxide. It a 6-thia compound is being oxidized to the sulfoxide or the sulfoxide to the sulfone, then about one equivalent of oxidizing agent should be used; if the 6-thia compound is being oxidized to the sulfone, then at least two equivalents of oxidizing agent should be used.

This oxidation usually yields the sulfoxide cleanly, but further oxidation to the sulfone often causes oxide formation also at the N of the fused pyridine ring, so that the sulfone will need to be separated from sulfone-N-oxide.

SCHEME E:

An alkyl substituent $R^1$ or $R^2$ may be introduced into a compound of Formula I at the 5-position, provided that the 5-carbon atom is activated. The reaction can be effected with an alkylating agent such as an alkyl halide, e.g., the iodide, and a base, e.g., sodium hydride, in an inert anhydrous organic solvent such as DMF:

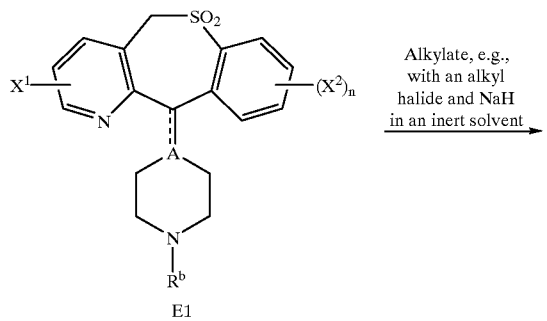

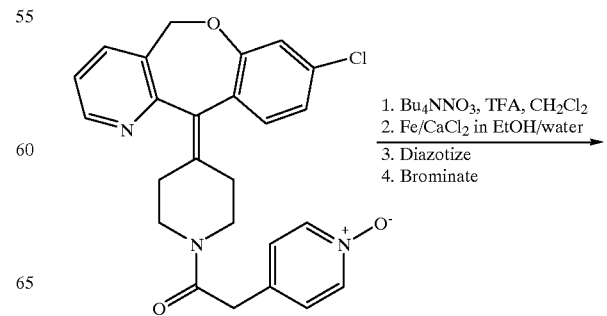

13

-continued

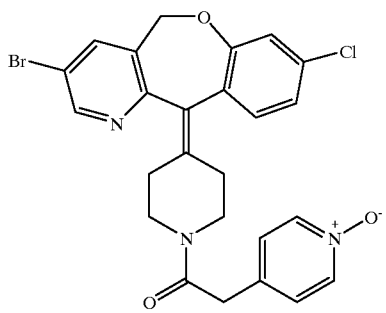

SCHEME G:

A compound in which $R^b$ is a protecting group or a hydrogen atom can be converted into a compound wherein R is —CZ-$Y^1$—$Y^2$—$R^3$, wherein Z, $Y^1$, $Y^2$, and $R^3$ are as defined for Formula I. When $R^b$ is hydrogen, the reaction can be effected by simple condensation, e.g., amidation with the acid in the presence of a dehydrating agent or with a reactive derivative of the acid.

A protecting group $R^b$ should normally be removed before the group R is introduced. When $R^b$ is methyl, it can be replaced by ethoxycarbonyl by reaction with ethyl chloroformate; an ethoxycarbonyl group can be removed by hydrolysis, e.g., with alkali such as alcoholic KOH or with concentrated HCl.

The group R can also be introduced by condensation of a compound of the formula A3, wherein $R^b$ is hydrogen, with a compound of the formula R-Hal, where Hal is Br or preferably Cl, in the presence of a strong base, e.g., a tertiary amine such as N,N-di(2-propyl)ethylamine, and an inert organic solvent such as acetonitrile at a moderate temperature such as 60–100° C.

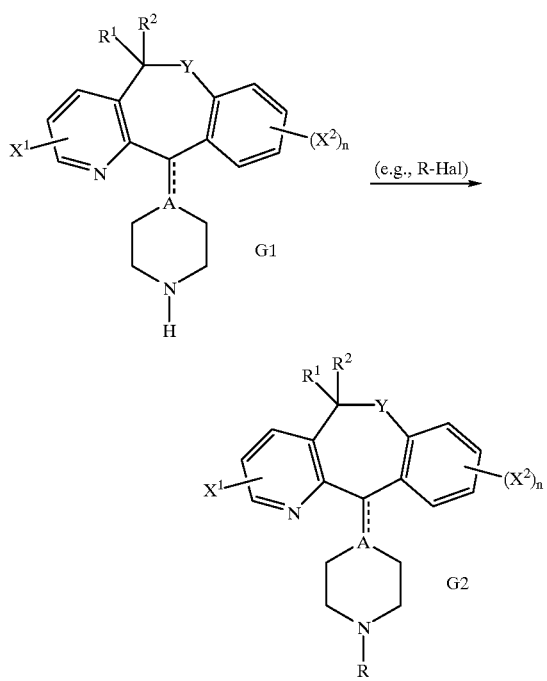

SCHEME H:

A compound wherein $R^3$ is a heterocycloalkyl group including an —NH— group can be converted into the corresponding urea, i.e., the compound wherein $R^3$ is a heterocycloalkyl group including an —N(CONH$_2$)— group, by heating in aqueous solution, preferably at 95–100° C., with urea (preferably in large excess, e.g., 10 equivalents). This process is illustrated for a compound of the invention in the following scheme, but is not restricted to this embodiment:

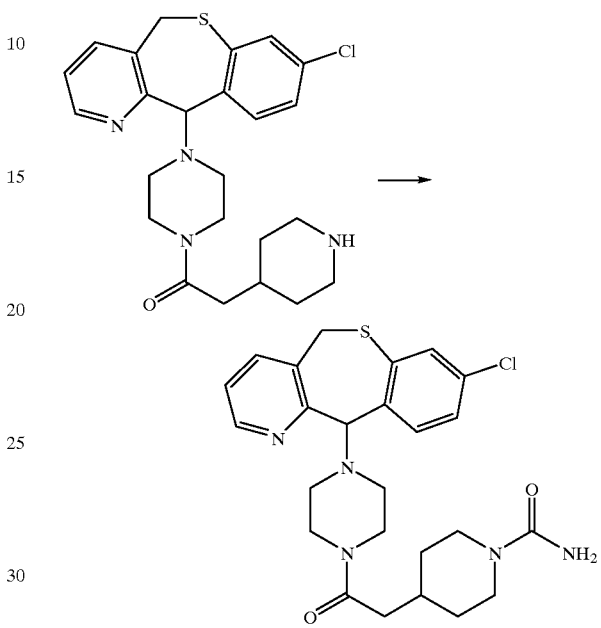

PREPARATIONS AND EXAMPLES

The following Examples (and Preparations) illustrate but do not in any way limit the present invention. Standard abbreviations and formulae are used throughout the Examples and Preparations, as well as the following:

EDCl and DEC are 1-(3-diethylaminopropyl)-3-ethylcarbodiimide;
HOBT is 1-hydroxy-benzotriazole monohydrate;
NMM is N-methyl-morpholine;
(MeS)$_2$C=NCN is dimethyl N-cyanodithio-iminocarbonate;
TMSNCO is trimethylsilylisocyanate;
TFA is trifluoroacetic acid;
TLC is thin layer chromatography;
M represents the molecular ion of the molecule in the mass spectrum;
M+H represents the molecular ion of the molecule plus hydrogen in the mass spectrum.

The preparation of compounds of the formula Al (see Scheme A above), e.g., 8-chloro-5,11-dihydro[1]benzoxepino[4,3-b]pyridin-11-one

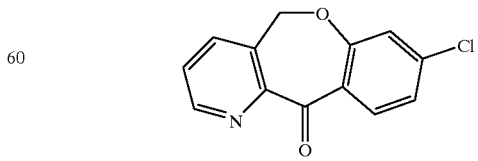

and its 10-chloro isomer, is given in PCT application WO 89/10369, in the corresponding U.S. Pat. No. 5,104,876 (see also Chem. Abs. (1990) 112, 178941b), and in *J. Med. Chem.*, 1995, 38, pp. 496–507 (Iwasaki et al.). These references also show the preparation of various other compounds usable as starting materials, e.g., of 4-(8-chloro-5,11-dihydro[1]benzothiepino[4,3-b]pyridin-11-ylidene)-piperidine (see, e.g., Preparative Example 7 of U.S. Pat. No. 5,104,876) and ethyl 4-(8-chloro-5,11-dihydro[1]benzoxepino[4,3-b]pyridin-11-ylidene)-1-piperidine-carboxylate (see, e.g., Preparative Example 4 of U.S. Pat. No. 5,104,876).

PREPARATION 1

1-(8-Chloro-5 11-dihydro[1]benzoxepino[4,3-b]pyridin-11-yl)-piperazine

Step A: 8-Chloro-5,11-dihydro[1]benzoxepino[4,3-b]pyridin-11-ol

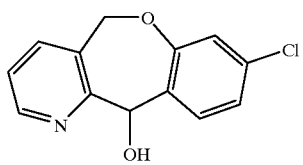

NaBH₄ (4.0 g, 1.06 mmol) was added to a solution of 5,1 1-dihydro-[1]benzoxepino[4,3-b]pyridin-11-one (20 g, 81.6 mmol) in ethanol (USP, 200 ml) at 0° C. The solution was stirred at 0° C. and then at 10° C. for two hours. The ethanol was evaporated off and the residue was extracted with CH₂Cl₂ (300 ml) and water (200 ml). The CH₂Cl₂ extract was dried (MgSO₄), filtered, and evaporated. The resulting syrup was largely dissolved in ether (about 20 ml) and acetone was added, yielding crystals of 8-chloro-5,1 1-dihydro[1]benz-oxepino[4,3-b]pyridin-11-ol. These were filtered off, washed with ether and hexanes and dried, m.p. 107–109° C.; MS (CI, M+H)=248; yield 16.39 g.

Step B: 1-(8-Chloro-5,11-dihydro[1]benzoxepino[4,3-b]pyridin-11-yl)-piperazine

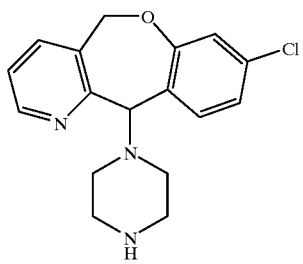

Thionyl chloride (4.5 g) in toluene (5 ml) was added to a suspension of 8-chloro-5,11-dihydro[1]benzoxepino[4,3-b]pyridin-11-ol(9 g, 36.4 mmol) in toluene (195 ml) at −5° C., and the mixture was stirred 3½ hours at −5° C. Water (100 ml), 10% NaOH (50 ml) and EtOAc (100 ml) were added, and the organic layer was separated, washed with water, dried (MgSO₄), filtered and evaporated. The residue was dissolved in ether (100 ml), and the solution was filtered and evaporated, yielding a reddish oil (about 9 g), which was used without further purification.

8,11-Dichloro-5,11-dihydro[1]benzoxepino[4,3-b]pyridine (9.0 g, 33.8 mmol), piperazine (3.4 g, 40.6 mmol), N,N-di(2-propyl)ethylamine (8 ml, 45.8 mmol) and acetonitrile (200 ml) were mixed and refluxed overnight. The reaction mixture was cooled to 40° C., water (50 ml) was added, and the resulting yellow precipitate (about 4 g) was filtered off. The aqueous phase was extracted with methylene chloride, and the organic solution was washed with water (15 ml), dried (MgSO₄), filtered and evaporated, yielding a yellow syrup (about 6 g). This was combined with the yellow precipitate (about 4 g; total about 10 g), and the total product was chromatographed on silica and eluted with 10%MeOH/EtOAc/NH₄OH and then with 15%MeOH/EtOAc/3%-NH₄OH. The resulting purified product was recrystallized from acetone/ether to afford a white powder, 1-(8-chloro-5,11-dihydro[1]benzoxepino[4,3-b]pyridin-11-yl)-piperazine, which was dried at room temperature and 0.2 mm: yield 3.3 g; m.p. 162–163° C.; MS (CI, M+H)=316; anal.: Found: C, 64.79; H, 5.93; N, 13.10; C₁₇H₁₈ClN₃O requires: C, 64.65; H, 5.74; N, 13.30.

PREPARATION 2

4-(3-Bromo-8-chloro-5,11-dihydro[1]benzoxepino[4,3-b]pyridin-11-ylidene)-1-piperidine Step A: Ethyl 4-(8-chloro-5,11-dihydro-3-nitro[1]benzoxepino[4,3-b]pyridin-11-ylidene)-1-piperidine-carboxylate

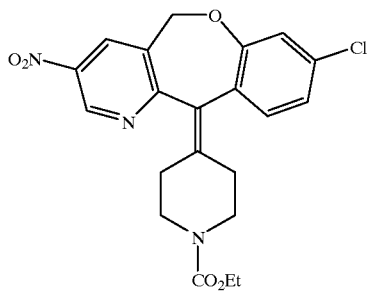

A solution of tetrabutylammonium nitrate (1.58 g, 5.19 mmol) in methylene chloride (10 ml) was added dropwise to a solution of ethyl 4-(8-chloro-5,11-dihydro[1]benzoxepino[4,3-b]pyridin-11-ylidene)-1-piperidine-carboxylate (2.0 g., 5.2 mmol) and trifluoroacetic anhydride (0.73 ml, 5.16 mmol) in methylene chloride (25 ml). The solution was stirred overnight at 20° C.

The reaction mixture was basified to pH 14 with 10% sodium hydroxide, and the organic layer was separated, dried (MgSO₄), filtered, and evaporated, yielding an oil which was chromatographed on silica gel and eluted with 20% ethyl acetate/hexanes. The resulting solid was recrystallized from methanol/ether to afford white crystals of ethyl 4-(8-chloro-5,11-dihydro-3-nitro[1]benzoxepino[4,3-b]pyridin-11-ylidene)-1-piperidine-carboxylate, m.p. 192–193° C. MS (CI, M+H)=430; anal.: found: C, 58.15; H, 4.84; N, 9.78; C₂₁H₂₀ClN₃O₅ requires: C, 58.67; H, 4.69; N, 9.77.

Step B: Ethyl 4-(3-amino-8-chloro-5,11-dihydro[1]benzoxepino[4,3-b]pyridin-11-ylidene)-1-piperidine-carboxylate

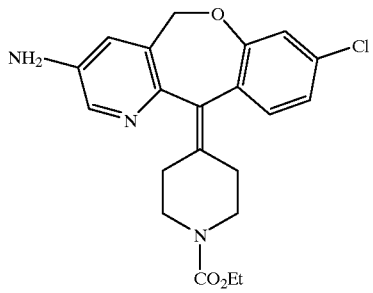

Iron powder (10 g., 0.179 Mol) and CaCl₂ (2 g, 18.0 mmol) were added to a suspension of ethyl 4-(8-chloro-5,11-dihydro-3-nitro[1]benzoxepino[4,3-b]pyridin-11-ylidene)-1-piperidine-carboxylate (10 g, 23.2 mmol) in ethanol:water (10:1 v/v, 200 ml), and the mixture was stirred at 60° C. for 3 hours.

The reaction mixture was concentrated, extracted with methylene chloride (600 ml), and filtered through a 'Celite' pad. The filtrate was washed with water (200 ml), dried (MgSO₄), filtered, and evaporated, and the resulting oil was chromatographed on silica gel and eluted with 5%MeOH/ethylacetate, yielding the product, ethyl 4-(3-amino-8-chloro-5,11-dihydro[1]benzoxepino[4,3-b]pyridin-11-ylidene)-1-piperidine-carboxylate, as a black solid (3.4 g, 36%), m.p. 133° C. (dec.). MS (CI, M+H)=400.

Step C: Ethyl 4-(3-bromo-8-chloro-5,11 -dihydro[1] benzoxepino[4,3-b]pyridin-11-ylidene)-1-piperidine-carboxylate

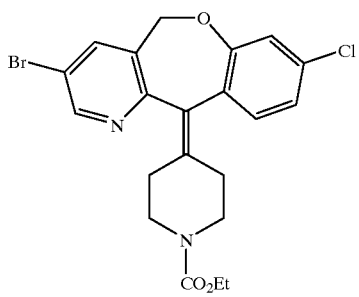

Bromine (1.0 ml, 19.4 mmol) was added to a suspension of ethyl 4-(3-amino-8-chloro-5,11-dihydro[1]benzoxepino[4,3-b]pyridin-11-ylidene)-1-piperidine-carboxylate (1.5 g, 3.75 mmol) in hydrobromic acid (150 ml) at 0° C. for 10 minutes. Sodium nitrite (0.7 g, 10.14 mmol) in water (5 ml) was added at 0° C., and the mixture was stirred at 0° C. for 1 hour and then at 20° C. for 2 hours. The reaction mixture was poured onto ice (200 g), basified with concentrated ammonium hydroxide and extracted with ethyl acetate (500 ml). The organic layer was washed with water (300 ml), dried (MgSO₄), filtered and evaporated, yielding a crude product which was chromatographed on silica gel and eluted with 30%ethylacetate/hexanes. The product was recrystallized from ether to afford a white powder, ethyl 4-(3-bromo-8-chloro-5,11-dihydro[1]benz-oxepino[4,3-b]pyridin-11-ylidene)-1-piperidine-carboxylate (1.0 g, 58%), m.p. 148–149° C. MS (CI, M+H)=463; anal.: found: C, 53.92; H, 4.16; N, 6.18; $C_{21}H_{20}BrClN_2O_3$ requires: C, 54.38; H, 4.34; N, 6.04.

Step D: 4-(3-Bromo-8-chloro-5,11-dihydro[1]benzoxepino [4,3-b]pyridin-11-ylidene)-1-piperidine

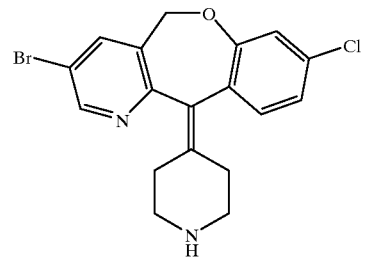

A solution of ethyl 4-(3-bromo-8-chloro-5,11 -dihydro[1]benzoxepino[4,3-b]pyridin-11-ylidene)-1-piperidine-carboxylate (0.8 g, 1.72 mmol) in conc. HCl (5 ml) was stirred at 80° C. for 3 days. The reaction mixture was cooled to room temperature, poured onto ice (20 g), and basified at 0° C. with conc. NH₄OH. The precipitate was filtered off, washed with water (10 ml), and dried at 20° C./0.2 mm to afford 4-(3-bromo-8-chloro-5,11-dihydro[1]benzoxepino[4,3-b]pyridin-11-ylidene)-1-piperidine (0.6 g, 88%); MS (CI, M+H)=391.

PREPARATION 3

4-(9-Bromo-8-chloro-5,11-dihydro[1]benzoxepino [4,3-b]pyridin-11-ylidene)-piperidine Step A: Ethyl 4-(9-bromo-8-chloro-5,11-dihydro[1] benzoxepino[4,3-b]pyridin-11-ylidene)-1-piperidine-carboxylate

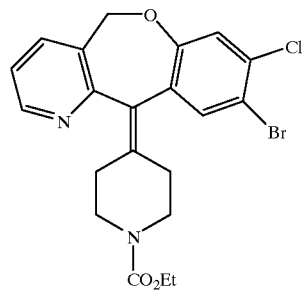

Bromine (0.5 ml, 9.7 mmol) was added to a solution of ethyl 4-(8-chloro-5,11-dihydro[1]benzoxepino[4,3-b] pyridin-11-ylidene)-1-piperidine-carboxylate (1.0 g., 2.6 mmol) in methylene chloride (15 ml) at 20° C. The solution was stirred for 2 hours at 20° C. The reaction mixture was poured onto ice (50 g), basified with 10% NaOH, and extracted with methylene chloride (100 ml). The organic layer was separated, washed with water (20 ml), dried (MgSO₄), filtered and evaporated, yielding an oil which was chromatographed on silica gel and eluted with 1:1 ethylacetate/hexanes. The product, ethyl 4-(9-bromo-8-chloro-5,11-dihydro[1]benzoxepino[4,3-b]pyridin-11-ylidene)-1-piperidine-carboxylate (0.8 g., 66% yield) was obtained as a white solid; MS (CI, M+H)=465.

Step B: 4-(9-Bromo-8-chloro-5,11-dihydro[1]benzoxepino [4,3-b]pyridin-11-ylidene)-piperidine

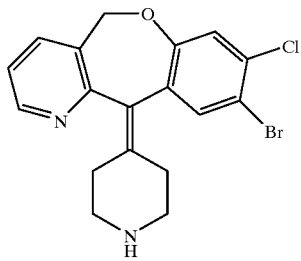

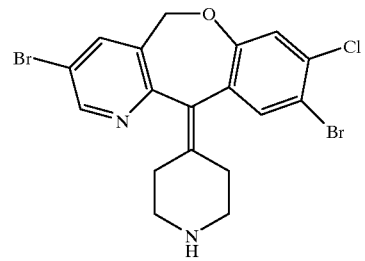

A solution of ethyl 4-(9-bromo-8-chloro-5,11-dihydro[1]benzoxepino[4,3-b]pyridin-1 1-ylidene)-1-piperidine-carboxylate (0.6 g, 1.29 mmol) in conc. HCl (5 ml) was stirred at 80° C. overnight. The reaction mixture was cooled to 0° C., basified with conc. NH$_4$OH, and extracted with methylene chloride (2×100 ml). The organic layer was separated, washed with water (20 ml), dried (MgSO$_4$), filtered and evaporated, yielding an oil which was chromatographed on silica gel and eluted with 10%methanol/ethylacetate containing 2% conc. NH$_4$OH. The product, 4-(9-bromo-8-chloro-5,11-dihydro[1]benzoxepino[4,3-b]pyridin-11-ylidene)-piperidine (470 mg., 93% yield) was obtained as a white solid, m.p. 198–199° C.; MS (CI, M+H)=391; anal.: found: C, 55.32; H, 4.15; N, 7.12; C$_{18}$H$_{16}$BrClN$_2$O requires: C, 55.19; H, 4.31; N, 7.15.

PREPARATION 4

4-(3,9-Dibromo-8-chloro-5,11-dihydro[1]benzoxepino[4,3-b]pyridin-11-ylidene)-piperidine Step A: Ethyl 4-(3,9-dibromo-8-chloro-5,11-dihydro[1]benzoxepino[4,3-b]pyridin-11-ylidene)-1-piperidine-carboxylate

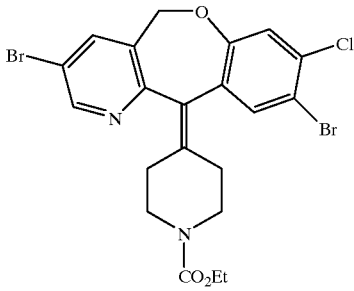

Ethyl 4-(3,9-dibromo-8-chloro-5,11-dihydro[1]benzoxepino[4,3-b]pyridin-11-ylidene)-1-piperidine-carboxylate (m.p. 153–155° C.; MS (CI, M+H)=541) could be prepared by the method of Preparation 3 Step A from ethyl 4-(3-bromo-8-chloro-5, 11-dihydro[1]benzoxepino[4,3-b]pyridin-11-ylidene)-1-piperidine-carboxylate.

Step B: 4-(3,9-Dibromo-8-chloro-5,11-dihydro[1]benzoxepino[4,3-b]pyridin-11-ylidene)-piperidine 4-(3,9-Dibromo-8-chloro-5,11-dihydro[1]benzoxepino[4,3-b]pyridin-11-ylidene)-piperidine could be prepared by the method of Preparation 3 Step B from ethyl 4-(3,9-dibromo-8-chloro-5,11-dihydro[1]benzoxepino[4,3-b]pyridin-11-ylidene)-1-piperidine-carboxylate.

PREPARATION 5

4-(8-Chloro-5,11-dihydro-[1]benzothiepino[4,3-b]pyridin-11-ylidene)-piperidine and 4-(10-chloro-5,11-dihydro-[1]benzothiepino[4,3-b]pyridin-11-ylidene)-piperidine Step A: 3-[(3-Chlorophenyl)thiomethyl]-2-pyridinecarboxylic acid

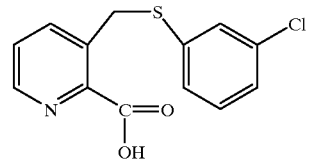

A mixture of 3-[(3-chlorophenyl)thiomethyl]-2-cyanopyridine (7.5 g, 28.8 mmol; see U.S. Pat. No. 5,104,876, Preparative Example 7), 25% NaOH (50 ml) and 30% hydrogen peroxide (2 ml) was heated at 110° C. for 2 days and then cooled to room temperature. Water was added, and the mixture was acidified with concentrated HCl to pH 6.5. The water was removed under reduced pressure and the resulting solid was extracted with boiling MeOH/THF (9:1). The organic extracts were evaporated to dryness and chromatographed on silica gel to afford analytically pure material; MS (CI, M+H)=280.1.

Step B: 3-[(3-Chlorophenyl)thiomethyl]-N-methoxy-N-methyl-2-pyridine-carboxamide

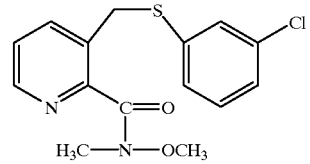

N-Methoxymethylamine (1.05 g) was dissolved in THF-water (25:1, 5 ml) with anhydrous K$_2$CO$_3$ (1.5 g), and the solution was stirred at room temperature for 30 minutes. It was then transferred by syringe into a flask containing 3-[(3-chlorophenyl)thiomethyl]-2-pyridinecarboxylic acid (2.0 g, 7.16 mmol) in a mixture of THF (3 ml), DMF (2 ml) and NMM (0.5 ml). HOBT (180 mg, 1.33 mmol) and EDCI (255 mg, 1.33 mmol) were added at 0° C. and the mixture was then stirred 28 hours at room temperature. The reaction mixture was diluted with water and extracted with EtOAc. The extracts were washed with brine, dried (Na₂SO₄), filtered and concentrated. The product was chromatographed on silica in 2%MeOH/CH₂Cl₂ and afforded 200 mg of 3-[(3-chlorophenyl)thiomethyl)]-N-methoxy-N-methyl-2-pyridinecarboxamide; MS (EI, M)=292; MS (CI, M+H)=293.

Step C: [3-[(3-Chlorophenyl)thiomethyl]-2-pyridinyl][1-methyl-4-piperidinyl]methanone

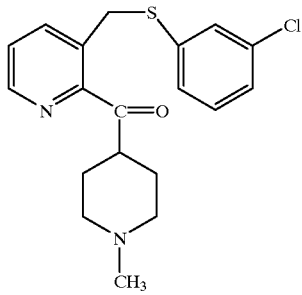

Anhydrous CeCl₃ (1.1 g, 4.46 mmol) was placed in a 50 ml 2-necked flask and flamed out under vacuum. The vacuum was replaced with N₂, and dry THF (20 ml) was added. The CeCl₃/THF solution was stirred at room temperature for 16 hours and then cooled to −40° C., and the Mg-Grignard reagent from 4-chloro-1-methyl-piperidine (3 ml of an 0.8M stock solution in THF) was added. The resulting solution was stirred at −40° C. for 75 minutes, and then 3-[(3-chlorophenyl)thiomethyl]-N-methoxy-N-methyl-2-pyridinecarboxamide (345 mg, 1.07 mmol) was added dropwise. After 40 minutes, the mixture was poured into 5% HCl/EtOAc, stirred for 5 minutes, and then basified to pH ~8. The organic product was extracted with EtOAc (6×100 ml), the extracts were washed with brine, dried (Na₂SO₄), filtered and concentrated. The product was chromatographed on silica and eluted with 5–10%MeOH/CH₂Cl₂ to afford [3-[(3-chlorophenyl)thiomethyl]-2-pyridinyl][1-methyl-4-piperidinyl]methanone (251 mg, 64%); HRMS, FAB, calcd. 361.1141; found. 361.1141.

Step D: 4-(8-Chloro-5,11-dihydro[1]benzothiepino[4,3-b]pyridin-11-ylidene)-1-methyl-piperidine and 4-(10-Chloro-5,11-dihydro[1]benzothiepino[4,3-b]pyridin-11-ylidene)-1-methyl-piperidine

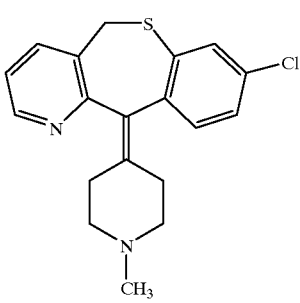

and

-continued

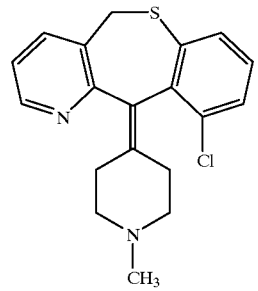

Polyphosphoric acid (40 g) and [3-[(3-chlorophenyl)thiomethyl]-2-pyridinyl][1-methyl-4-piperidinyl]methanone (650 mg, 180 mmol) were mixed at room temperature in a flask and then heated in an oil bath at 175° C. After 16 hours, the reaction mixture was poured onto crushed ice containing 5% NaOH. More water was added, and the solution was stirred until homogeneous. It was then cooled to 0° C., and 50% NaOH was added to a pH of 10–11 (about 50–60 ml). The aqueous mixture was then extracted with EtOAc (6×200 ml). The combined EtOAc extracts were washed with brine, dried (Na₂SO₄), filtered, concentrated, and chromatographed on silica. The products were as follows:

4-(8-Chloro-5,1 1-dihydro[1]benzothiepino[4,3-b]pyridin-11-ylidene)-1-methyl-piperidine, 79 mg; MS (CI, M+H)=343;

an unresolved mixture of that compound and the next, 110 mg;

4-(10-Chloro-5,11-dihydro[1]benzothiepino[4,3-b]pyridin-11-ylidene)-1-methyl-piperidine, 51 mg; MS (CI, M+H)=343; and 4-(8-Chloro-5,11-dihydro-11-hydroxy-[1]benzothiepino[4,3-b]pyridin-11-yl)-1-methyl-piperidine, 177 mg.

Step E: Ethyl 4-(8-chloro-5,11-dihydro-[1]benzothiepino[4,3-b]pyridin-11-ylidene)-piperidine-1-carboxylate

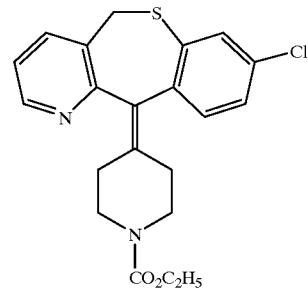

4-(8-Chloro-5,11-dihydro-[1]benzothiepino[4,3-b]pyridin-11-ylidene)-1-methylpiperidine (840 mg, 2.45 mmols) was dissolved in toluene (30 ml), and ClCO₂Et (3 ml, 3.4 g, 31.5 mmols). Et₃N (1 ml) was added, and the mixture was heated at 80° C. for 1.5 hour. The mixture was cooled to room temperature, and NaOH solution (50%, 50 ml) and water (50 ml) were added. The aqueous phase was extracted with EtOAc (5×100 ml). The combined organic phases were washed with brine, dried (MgSO4), filtered and concentrated. The product was chromatographed on silica to afford an amber amorphous solid, 658 mg; found: C, 63.04; H, 5.53; N, 6.69; Cl, 7.66; S, 8.67; calcd. for C₂₁H₂₁ClN₂O₂S: C, 62.91; H, 5.28; N, 6.99; Cl, 8.00; S, 8.84.

Step F: 4-(8-Chloro-5,11-dihydro[1]benzothiepino[4,3-b]pyridin-11-ylidene)-piperidine

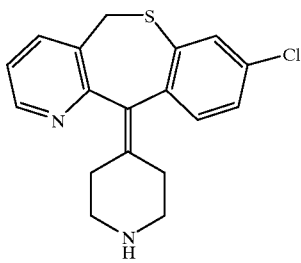

Ethyl 4-(8-chloro-5,11-dihydro[1]benzothiepino[4,3-b]pyridin-11-ylidene)-piperidine-1-carboxylate (600 mg, 1.50 mmol) and KOH (4.5 g, 80.3 mmol) were dissolved in ethanol (50 ml) and water (40 ml), and the mixture was refluxed for 8 hours. The mixture was stirred under reflux overnight and cooled to room temperature; the ethanol was evaporated off and the residual mixture was neutralized with 10% HCl to pH ~8. The liquid was extracted with $CH_2Cl_2$, the extract was washed with brine, dried ($MgSO_4$), filtered and concentrated to afford a tan solid (475 mg) which contained a 6:1 ratio of product to starting material by NMR. Chromatography on silica gel using 5%MeOH/$CH_2Cl_2$ gave 374 mg (75%) of an off-white solid, m.p. 216–218° C.; MS (CI, M+H)=389; anal.: found: C, 60.40; H, 5.58; N, 6.83; S, 7.87; $C_{18}H_{17}ClN_2S\cdot\frac{1}{2}H_2O$ requires: C, 60.45; H, 5.29; N, 7.05; S, 8.06.

Steps G and H: Ethyl 4-(10-chloro-5,11-dihydro-[1]benzothiepino[4,3-b]pyridin-11-ylidene)-piperidine-1-carboxylate and 4-(10-chloro-5,11-dihydro-[1]benzothiepino[4,3-b]pyridin-11-ylidene)-piperidine.

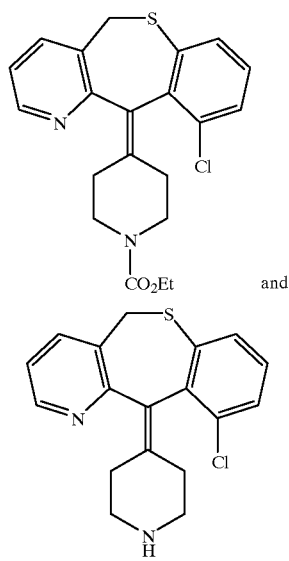

These compounds were prepared according to the methods of Preparation 5 Steps E and F from 4-(10-chloro-5,11-dihydro[1]benzothiepino[4,3-b]pyridin-11-ylidene)-1-methyl-piperidine.

PREPARATION 6

1-(8-Chloro-5,11-dihydro-[1]benzothiepino[4,3-b]pyridin-11-yl)-piperazine

Step A1: 8-Chloro-[1]-benzothiepino[4,3-b]pyridin-11-(5H)-one

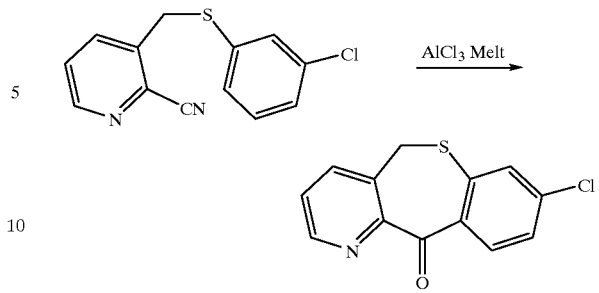

3[[(3-chlorophenyl)thio]methyl]-2-pyridinecarbonitrile (3.0 g, 11.5 mmols, see U.S. 5,104,876, Preparative Example 7) was mixed in a mortar and pistle with $AlCl_3$ (7.6 g). The powered mixture was transferred to a 100 mL flask fitted with a condenser and heated between 160–180° C. for 45 min. upon which the yellow solid melted into a deep red viscous liquid. After cooling to room temperature, 6N HCl (60 mL) was slowly and carefully added. The acidified mixture was heated to 60° C. for 30 min, then cooled to 0° C. and basified to pH=14 with 25% NaOH. The mixture was extracted with EtOAc (4×150 mL) and once with 15% THF-EtOAc. The combined organics were washed with brine, dried over $MgSO_4$, filtered and concentrated to give 2.88 g of crude material. Chromatography on silica gel (20% EtOAc-hexane increasing to 10% MeOH-$CH_2Cl_2$) afforded 2.44 g (81%) of pure material as a light brown solid. Decolorization with activated carbon in acetone provides a fluffy white solid, MP =189.5–190.2° C. Irms (EI, M$^+$)=261.

Step A2: 8-Chloro-5,11-dihydro[1]benzothiepino[4,3-b]pyridin-11-ol

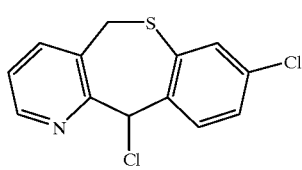

8-Chloro-5,11-dihydro[1]benzothiepino[4,3-b]pyridin-11-one (5.02 g, 19.2 mmol; from Step A1) was dissolved in methanol (80 ml) at room temperature, and $NaBH_4$ (871 mg, 23 mmol) was added. The reaction mixture was stirred one hour at room temperature and then was evaporated to dryness. The red residue was dissolved in $CH_2Cl_2$ and water, and the aqueous layer was further extracted with $CH_2Cl_2$ (3×80 ml). The combined organic phase was washed with brine, dried ($Na_2SO_4$) and decanted. The product (4.39 g, 87%), which was isolated by flash chromatography (20%hexane/$CH_2Cl_2$, changing to $CH_2Cl_2$), was used direct in the next step.

Step B: 8,11-Dichloro-5,11-dihydro[1]benzothiepino[4,3-b]pyridine

8-Chloro-5,11-dihydro[1]benzothiepino[4,3-b]pyridin-11-ol (164 mg, 0.62 mmol) was combined with $CH_2Cl_2$ (5 ml) in a flame-dried round-bottom flask, and the mixture was cooled to 0° C. in an ice-bath. SOCl₂ (0.06 ml, 0.81 mmol) was added by syringe, and a yellow suspension formed. The reaction mixture was stirred for two hours at room temperature. NaOH (~20 ml, 2.5M) was added by pipette, and the mixture was stirred vigorously for 10 minutes. The layers were separated, and the aqueous layer was further extracted with CH₂Cl₂ (3×20 ml). The combined organic phase was washed with brine, dried (Na₂SO₄), decanted and concentrated to afford a crude product, 175 mg, which was shown by NMR to be about 82% 8,11-dichloride (145 mg) and about 12% 11-ol (starting material and was used direct in the next step.

Step C: 1-(8-Chloro-5,11-dihydro-[1]benzothiepino[4,3-b]pyridin-11-yl)-piperazine

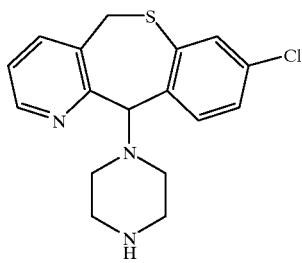

A slurry of 8,11-dichloro-5,11-dihydro-[1]benzothiepino[4,3-b]pyridine (3.79 g, 13.43 mmol) in THF (25 ml) was added dropwise to piperazine (3.53 g, 157 mmol) in THF (50 ml) over 45 minutes. The mixture was stirred at room temperature for 5 hours and the reaction was then quenched with the slow addition of NaOH (200 ml, 2.5N) and extracted with CH₂Cl₂ (400 ml and 4×100 ml). The combined organic layers were washed with brine, dried (Na₂SO₄), decanted and concentrated; the crude product was purified by flash chromatography (10%acetone/CH₂Cl₂ to 10%MeOH/CH₂Cl₂/NH₄OH) and obtained as a white solid (4.08 g, 91%); MS (FAB, M+H)=332; found: C, 61.73; H, .5.60; N, 12.40; C₁₇H₁₈ClN₃S requires: C, 61.53; H, 5.47; N, 12.66.

PREPARATION 7

4-(8-Chloro-5,11-dihydro[1]benzothiepino[4,3-b]pyridin-11-ylidene)-piperidine-6,6-dioxide Step A: 4-(8-Chloro-5,11-dihydro[1]benzothiepino[4,3-b]pyridin-11-ylidene)-1-ethoxycarbonyl-piperidine-6,6-dioxide

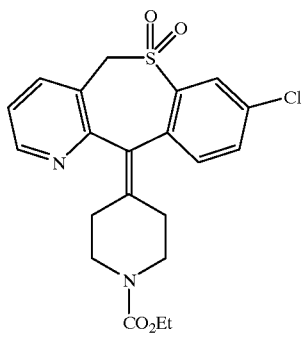

To 4-(8-chloro-5,11-dihydro[1]benzothiepino[4,3-b]pyridin-11-ylidene)-1-ethoxycarbonyl-piperidine (215 mg) in CH₂Cl₂ (3 ml) was added a solution of 0.5N methanesulfonic acid in CH₂Cl₂ (3 ml), and the mixture was cooled to 0° C. After 10 minutes, 3-chloroperbenzoic acid (380 mg) was added. After 30 minutes, the mixture was warmed to room temperature and further 3-chloro-perbenzoic acid (50 mg) was added. After a further 45 minutes, the mixture was poured into saturated Na₂CO₃ and extracted with CH₂Cl₂. The CH₂Cl₂ solution was washed with brine, dried (MgSO₄), filtered, and concentrated. The product was chromatographed on silica gel (EtOAc) to afford a white fluffy solid (171 mg, 73%); found: C, 57.00; H, 4.84; N, 6.24; Cl, 8.90; S, 6.94; calcd. for C₂₁H₂₁ClN₂O₄S.½H₂O: C, 57.14; H, 4.76; N, 6.35; Cl, 8.19; S, 7.25.

Step B: 4-(8-Chloro-5,11-dihydro[1]benzothiepino[4,3-b]pyridin-11-ylidene)-piperidine-6,6-dioxide

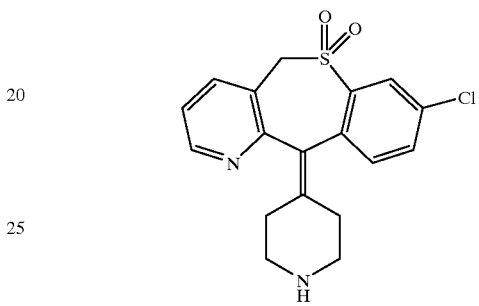

4-(8-Chloro-5,11-dihydro[1]benzothiepino[4,3-b]pyridin-11-ylidene)-1-ethoxycarbonyl-piperidine-6,6-dioxide (1.25 g, 2.89 mmols) and KOH (4 g) were dissolved in ethanol (25 ml) and water (15 ml), and the mixture was heated for 8 hours at 100° C. and then at 80° C. overnight. The mixture was cooled to room temperature; the ethanol was evaporated off and acid was added to the residual mixture to pH ~9. The liquid was extracted with CH₂Cl₂ (6×75 ml) and with CHCl₃ (3×50 ml), and the combined extracts were washed with brine, dried (MgSO₄), filtered and concentrated. The product was chromatographed on silica gel using 10%MeOH/CH₂Cl₂ initially, changing to 10%MeOH/CH₂Cl₂ containing 2% NH₄OH, to afford 989 mg (95%) of an off-white foam; MS (CI, M+H)=361.

PREPARATION 8

8-Chloro-5,11-dihydro[1]benzothiepino[4,3-b]pyridin-11-one-6-oxide

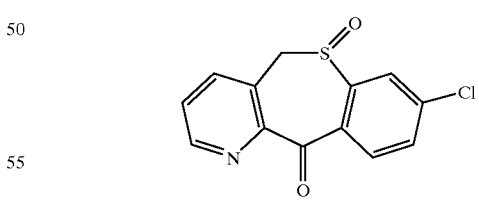

A solution of 8-chloro-5,11-dihydro[1]benzothiepino[4,3-b]pyridin-11-one (250 mg) in acetic acid (5 ml) was stirred for 5 minutes. NaBO₃ (105 mg) was added and the mixture was stirred for 7 hours. The reaction was quenched with 5% NaOH and extracted with CH₂Cl₂, and the extracts were washed with brine, dried (MgSO₄), filtered and concentrated to afford a tan solid (270 mg). This was chromatographed on silica to afford the crude sulfoxide (250 mg) as a tan solid containing some starting material; MS (CI, M+H)=278.

PREPARATION 9

4-(8-Chloro-5,11-dihydro-5,5-dimethyl-[1]
benzothiepino[4,3-b]pyridin-11-ylidene)-piperidine-
6,6-dioxide Step A: 8-Chloro-5,11-dihydro[1]benzothiepino[4,3-b]
pyridin-11-one-6,6-dioxide

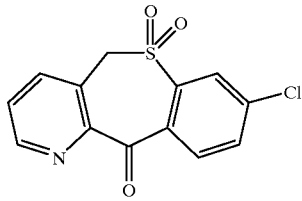

8-Chloro-5,11-dihydro[1]benzothiepino[4,3-b]pyridin-11-one-6-oxide (150 mg, 0.541 mmol) was dissolved in acetic acid (10 ml) and the solution was stirred 10 minutes. NaBO$_3$ (400 mg in 10 ml HOAc) was added and the mixture was stirred for 36 hours. The reaction was quenched with saturated Na$_2$CO$_3$ and extracted with CH$_2$Cl$_2$ (5×50 ml), and the extracts were washed with brine, dried (MgSO$_4$), filtered and concentrated. The residue was chromatographed on silica in 3%MeOH/CH$_2$Cl$_2$ and eluted with 5%MeOH/CH$_2$Cl$_2$ to afford the sulfone (120 mg, 76%) as a white solid; MS (CI, M+H)=294.

Step B: 8-Chloro-5,11-dihydro-5,5-dimethyl-[1]
benzothiepino[4,3-b]pyridin-11-one-6,6-dioxide

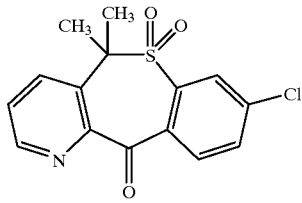

8-Chloro-5,11-dihydro[1]benzothiepino[4,3-b]pyridin-11-one-6,6-dioxide (475 mg, 1.62 mmol) in DMF (5 ml) was added dropwise at room temperature to a mixture of NaH (150 mg, 7.81 mmol) and DMF (12 ml) under N$_2$. The resulting mixture was stirred at room temperature for 1 hour and then cooled to 0° C. Methyl iodide (0.40 ml) was added, and then after 90 minutes further methyl iodide (0.40 ml) was added. The reaction mixture was stirred at room temperature overnight. The reaction was then quenched with MeOH, most of the DMF was evaporated off, and the residue was diluted with water and extracted with methylene chloride (5×50 ml). The combined organic layers were washed with brine, dried (MgSO$_4$), filtered and concentrated. The residue was chromatographed on silica, eluting with 30%acetone/hexane, to afford 8-chloro-5,11-dihydro-5,5-dimethyl-[1]benzothiepino[4,3-b]pyridin-11-one-6,6-dioxide (365 mg, 70%) as a light tan solid, m.p. 189–191° C.; MS (FAB, M+H)=322; anal.: found: C, 55.99; H, 3.76; N, 4.35; S, 9.96; Cl,11.02; C$_{15}$H$_{12}$ClNO$_3$S requires: C, 55.88; H, 3.85; N, 4.37; S, 9.68; Cl,11.36.

Step C: 8-Chloro-5,11-dihydro-11-hydroxy-5,5-dimethyl-[1]benzothiepino[4,3-b]pyridin-6,6-dioxide

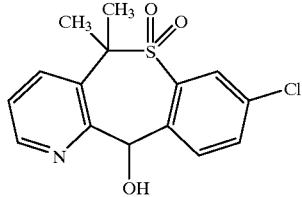

8-Chloro-5,11-dihydro-5,5-dimethyl-[1]benzothiepino[4,3-b]pyridin-11-one-6,6-dioxide (3.5 g, 0.109 mol) was dissolved in THF (140 ml), the solution was cooled to 0° C., and lithium aluminum hydride (350 mg, 9.22 mmol) was added in portions over 10 minutes. After 25 minutes, the reaction was quenched with MeOH/water (75 ml, 5:1), and the solvents were evaporated off. The residual material was diluted with water and NH$_4$Cl solution and extracted with EtOAc/THF (40:1). The organic extracts were washed with brine, dried (MgSO$_4$), filtered and concentrated to afford a light yellow solid (3.1 g, crude). Chromatography of this solid on silica in 10%EtOAc/CH$_2$Cl$_2$ gave the pure alcohol (2.9 g, 82%) as a light yellow solid; MS (FAB, M+H)=324.

Step D: 8-Chloro-5,11-dihydro-5,5-dimethyl-11-(1-methyl-piperidinylidene)-[1]benzothiepino[4,3-b]pyridine-6,6-dioxide

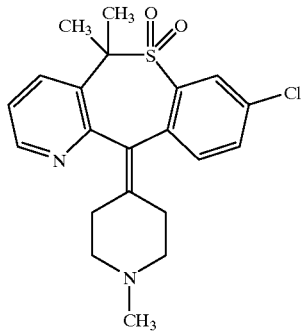

4-(8-Chloro-5,11-dihydro-5,5-dimethyl-11-hydroxy-[1]benzothiepino[4,3-b]pyridin-1 1-yl)-1-methyl-piperidine-6,6-dioxide (75 mg, 0.18 mmol) was dissolved in benzene, and Burgess reagent (methoxycarbonylsulfamoyltriethyl-ammonium hydroxide, 80 mg, 0.34 mmol) was then added. The mixture was heated to 70° C. for about 45 minutes and cooled to room temperature. Water and ammonium chloride solution were added, and the mixture was extracted with ethyl acetate. The extract was washed with brine, dried (MgSO$_4$), filtered and concentrated; the product was chromatographed on silica gel to afford a light yellow solid, 4-(8-chloro-5,11-dihydro-5,5-dimethyl-[1]benzothiepino[4,3-b]pyridin-11-ylidene)-1-methyl-piperidine-6,6-dioxide; MS (CI, M+H)=403.

Step E: 4-(8-Chloro-5,11-dihydro-5,5-dimethyl-[1]benzothiepino[4,3-b]pyridin-1 1-ylidene)-1-ethoxy-carbonyl-piperidine-6,6-dioxide

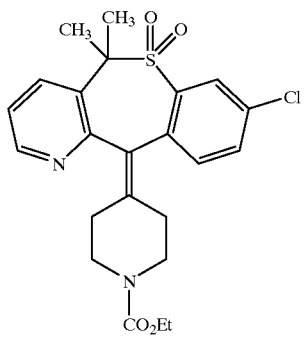

4-(8-Chloro-5,11-dihydro-5,5-dimethyl[1]benzothiepino[4,3-b]pyridin-11-ylidene)-1-methylpiperidine-6,6-dioxide (525 mg, 1.30 mmol) was dissolved in toluene (30 ml) at room temperature, and ethyl chloroformate (4 ml) and triethylamine (1 ml) were added. The reaction mixture was heated at 90° C. for 90 minutes and then cooled to room temperature; 5% NaOH (75 ml) was added, and the mixture was extracted with EtOAc (5×75 ml). The combined extracts were washed with brine, dried ($MgSO_4$), filtered and concentrated. The residue was chromatographed on silica (60%EtOAc/hexane, increasing to 100% EtOAc; then 5%MeOH/EtOAc) to afford an amber amorphous solid (313 mg, 52%); MS (CI, M+H)=461.

Step F: 4-(8-Chloro-5,11-dihydro-5,5-dimethyl-[1]benzothiepino[4,3-b]pyridin-1 1-ylidene)-piperidine-6,6-dioxide

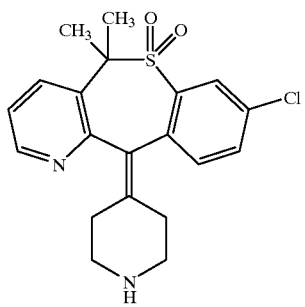

4-(8-Chloro-5,11-dihydro-5,5-dimethyl-[1]benzothiepino[4,3-b]pyridin-11-ylidene)-1-ethoxycarbonyl-piperidine-6,6-dioxide (300 mg, 0.65 mmol) was dissolved in a KOH solution (25 ml of a solution prepared from 5 g KOH, 20 ml water, and 25 ml ethanol) and the mixture was refluxed 6 hours. The mixture was cooled to room temperature and the solvents were evaporated off. The residue was diluted with water and with 1N HCl to pH ~11and extracted with $CH_2Cl_2$, and the extracts were washed with brine, dried ($MgSO_4$) filtered and concentrated to afford a crude product (220 mg). 100 mg of this product were purified on silica gel to afford the purified product, 62 mg; m.p. 178.5–182.5.

PREPARATION 10

1-(8-Chloro-5,11-dihydro-[1]benzothiepino[4,3-b]pyridin-11-yl)-piperazine-6-oxide

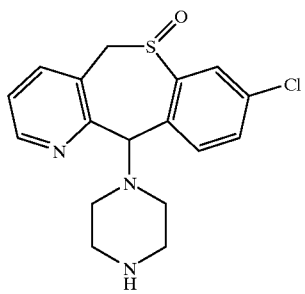

1-(8-Chloro-5,11-dihydro-[1]benzothiepino[4,3-b]pyridin-1 1-yl)-piperazine (500 mg, 1.51 mmol) was combined with anhydrous $CH_2Cl_2$ in a flame-dried flask, purged with nitrogen. The mixture was cooled to −42° C. in dry-ice/acetonitrile. 3-Chloroperbenzoic acid (759 mg, 3.52 mmol) was added, and the golden-brown mixture was stirred 70 minutes at −42° C. The reaction was quenched with 2.5M NaOH and the mixture allowed to warm to room temperature. More $CH_2Cl_2$ and 2.5M NaOH were added, and the layers were shaken and separated; the aqueous phase was extracted with $CH_2Cl_2$ (4×30 ml). The combined extracts were washed with brine, dried ($Na_2SO_4$), decanted and concentrated. The product was isolated by flash chromatography and eluted with 10%MeOH/$CH_2Cl_2$ and then with 10%MeOH/$CH_2Cl_2$/$NH_4OH$; 315 mg (60%) of 1-(8-chloro-5,11-dihydro-[1]benzothiepino[4,3-b]pyridin-11-yl)-piperazine-6-oxide.

PREPARATION 11

8-Chloro-6,11-dihydro-6-methyl-5H-pyrido[3,2-c][1]benzazepin-11-yl-piperazine

Step A: 2-Cyano-3-(N-methyl-3-chlorophenylaminomethyl)pyridine

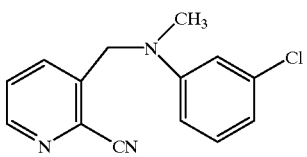

N-Methyl-3-chloroaniline (45 ml) and 2-cyano-3-chloromethylpyridine (37.6 g of a sample 62% pure, i.e., 23.4 g) were heated neat at 80–90° C. for 3 hours. The product was chromatographed on silica gel in hexane:$CH_2Cl_2$ 1:1. Three separate portions were collected; 13.9 g, 12.0 g, and 34.0 g, all of which were identified as the desired product. (During collection of the third portion, material seemed to solidify at the top of the column and interrupt flow; this part was scraped out and then the flow resumed.)

The 2-cyano-3-chloromethylpyridine was prepared by chlorination of 2-cyano-3-methylpyridine in chlorobenzene with benzoylperoxide by gradual addition of $SO_2Cl_2$ at 80° C. 2-Cyano-3-chloromethylpyridine was obtained in 60–65% conversion. The main impurities are 2-cyano-3-dichloromethylpyridine and unreacted 2-cyano-3-methylpyridine, which do not cause problems in the process of this Preparation.

Step B: 8-Chloro-6,11-dihydro-6-methyl-5H-pyrido[3,2-c][1]benzazepine-11-one and 10-chloro-6,11-dihydro-6-methyl-5H-pyrido[3,2-c][1]benzazepine-11-one

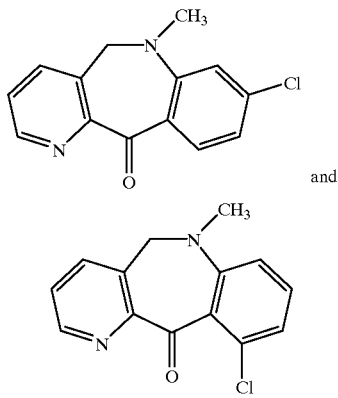

and

First Method $TiCl_4$ (16.38 g, 9.5 ml, 86.3 mmol) was added by syringe to 2-cyano-3-(N-methyl-3-chlorophenylaminomethyl) pyridine (11.12 g, 43.2 mmol) at 20° C., and the mixture was quickly heated to 100° C. and maintained there for 4 hours. A clear supernatant was decanted; the tar-like residue was acidified with 4N HCl and heated at 100° C. and was then stirred over the week-end at room temperature. The mixture was then basified with 4N NaOH to pH 9 and extracted once with EtOAc, then with $CH_2Cl_2$ (4 x) (NaCl being added to assist separation of phases), and finally again with EtOAc. The combined organic phases were evaporated to a residue, which was chromatographed on silica gel in $CH_2Cl_2$/EtOAc (95:5). After starting material (1.58 g) had been eluted, the 10-chloro isomer (3.37 g, 90% pure) was eluted, and finally the pure 8-chloro isomer (4.5 g). These were recrystallized from $CH_2Cl_2/Et_2O$; the following results were obtained:

10-Chloro isomer: m.p. 118.5–121.5° C.; found: C, 64.93; H, 4.41; N, 10.70; Cl,13.96; calcd. for $C_{14}H_{11}ClN_2O$: C, 65.00; H, 4.29; N, 10.83; Cl, 13.70.

8-Chloro isomer: m.p. 187–192° C.; found: C, 65.46; H, 4.47; N, 10.83; Cl, 13.57; calcd. for $C_{14}H_{11}ClN_2O$: C, 65.00; H, 4.29; N, 10.83; Cl,13.70.

Second Method

2-Cyano-3-(N-methyl-3-chlorophenylaminomethyl) pyridine (13.35 g) was ground in a pestle and mortar and dried overnight at 50° C. under vacuum. It was stirred with $AlCl_3$ (25.33 g) at room temperature; then the mixture was heated at 170–175° C. with stirring for 10 minutes. The crude product (12.58 g) was carefully dissolved in 1N HCl, first with cooling in ice and finally with heating at 70–80° C. for 75 minutes. The mixture was then basified and extracted with $CH_2Cl_2$. The product was chromatographed on silica gel in $CH_2Cl_2$ and eluted with $CH_2Cl_2$/EtOAc (95:5, 92:8, 9:1, and 8:2), and finally with $CH_2Cl_2$/MeOH (95:5 and 9:1). Early fractions (2.26 g) comprised the 10-chloro isomer; middle fractions (2.23 g) comprised a mixture of 8-chloro and 10-chloro isomers; and late fractions (6.37 g) comprised the 8-chloro isomer.

Step C: 8-Chloro-6,11-dihydro-6-methyl-5H-pyrido[3,2-c][1]benzazepin-11-ol

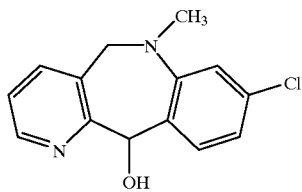

8-Chloro-6,11-dihydro-6-methyl-5H-pyrido[3,2-c][1]benzazepine-11-one (5.9 g) was dissolved with stirring in a mixture of $CH_2Cl_2$ and MeOH (60 ml, 1:4 v/v), and $NaBH_4$ (1.5 g) was added portionwise. After about 3 hours at room temperature, the solution was evaporated and the residue was partitioned between water and $CH_2Cl_2$. The layers were separated, and the aqueous layer was back-extracted with $CH_2Cl_2$ (2×20 ml). The combined organic layers were dried ($Na_2SO_4$), filtered and evaporated. The crude product was chromatographed on silica gel in hexane and eluted with hexane/EtOAc (7:3) to afford the title compound, 5.58 g (m.p. 112–114° C.); found: C, 65.12; H, 5.03; N, 10.74; calcd. for $C_{14}H_{13}ClN_2O$: C, 64.50; H, 5.03; N, 10.74.

Step D: 8-Chloro-6,11-dihydro-6-methyl-5H-pyrido[3,2-c][1]benzazepin-11-yl-piperazine

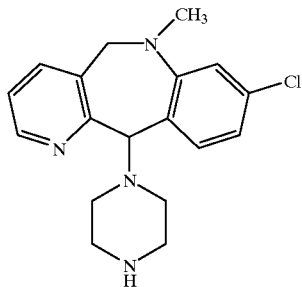

11-Hydroxy-8-chloro-6,11-dihydro-6-methyl-5H-pyrido[3,2-c][1]benzazepine (1.5 g, 5.77 mmol) and 4-dimethylaminopyridine (224 mg) were dissolved in pyridine (17 ml) at −4° C., and mesyl chloride (793 mg, 0.532 ml, 6.92 mmol, 1.2 equivalents) was added. More mesyl chloride (80 μl) was then added, and still more mesyl chloride (50 μl) after a further 1.5 hours. The reaction mixture was then added to a finely divided suspension of piperazine (2.5 g) in THF (17 ml) at room temperature, and the mixture was stirred overnight. The reaction mixture was then evaporated to a residue, and toluene (30 ml, twice) was added, and the solution was each time evaporated to a residue. The residue was then dissolved in $CH_2Cl_2$ and washed with water; the washings were back-extracted with $CH_2Cl_2$. The combined $CH_2Cl_2$ extracts were dried ($Na_2SO_4$), filtered and concentrated. The resulting dark syrup (2.53 g) was chromatographed on silica gel in $CH_2Cl_2$ and eluted with $CH_2Cl_2$/MeOH (97:3, then 93:7) and with $CH_2Cl_2$/MeOH/$NH_4OH$ (9:1:0.05, increasing to 9:1:0.2). A fraction of 1.07 g was obtained and triturated with $Et_2O$ and filtered; yield 545 mg. A sample (100 mg) was dissolved in $Et_2O$, filtered and concentrated to 25 ml and left to stand 3 days at 4° C.; hexane was then added to turbidity and the mixture was left overnight at 4° C. A precipitate was filtered off, and the solution was concentrated and afforded a white solid. HRMS, FAB, calcd. 329.1526; found 329.1533.

EXAMPLE 1

4-(8-Chloro-5,11-dihydro[1]benzoxepino[4.3-b]pyridin-11-yl)-1-(4-pyridine-acetyl)-piperazine N1-oxide

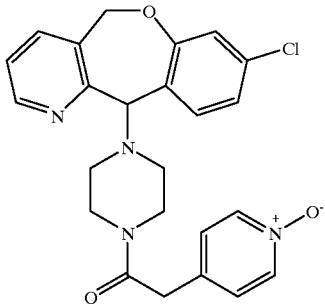

1-(8-Chloro-5,11-dihydro[1]benzoxepino[4,3-b]pyridin-11-yl)-piperazine (420 mg, 1.33 mmol), 4-pyridineacetic acid 1-oxide (280 mg, 2.07 mmol), HOBT (290 mg, 2.14 mmol), and EDCI (470 mg, 2.45 mmol) were stirred at 0C in DMF (5 ml, anhydrous). NMM (0.5 ml, 4.53 mmol) was added, and the reaction mixture was stirred overnight at 20° C. The solvent was evaporated off, and the residue was extracted with methylene chloride (200 ml) and water (100 ml). The organic layer was separated and dried (MgSO$_4$), filtered and evaporated, yielding an oil which was chromatographed on silica gel and eluted with 20%methanol/ethylacetate containing 2% ammonium hydroxide. The product was obtained as a light yellow solid, 4-(8-chloro-5,11-dihydro[1]benzoxepino[4,3-b]pyridin-11-yl)-1-(4-pyridine-acetyl)-piperazine N1-oxide. MS (FAB, M+H)=451.

EXAMPLE 2

Methyl [4-(8-chloro-5,11-dihydro[1]benzoxepino[4,3-b]pyridin-11-ylidene)-N-cyano-1-piperidinecarboximidothioate

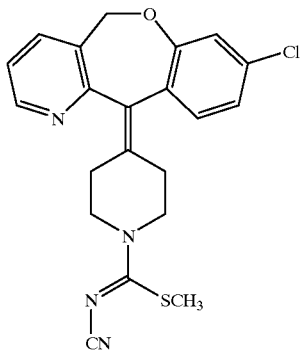

4-(8-Chloro-5,11-dihydro[1]benzoxepino[4,3-b]pyridin-11-ylidene)-piperidine (4.2 g, 13.5 mmol) and (MeS)$_2$C=NCN (4 g, 90%, 24.6 mmol) were dissolved in EtOH (UPS, 100 ml) at room temperature. The mixture was refluxed for 15 hours and then cooled, and the ethanol was evaporated off. The residue was chromatographed on silica and eluted with 30%EtOAc/hexanes to afford 4.2 g (76%) of a white solid, methyl [4-(8-chloro-5,11-dihydro[1]benzoxepino[4,3-b]pyridin-1 1-ylidene)-N-cyano-1-piperidinecarboximidothioate; MS (CI, M+H)=411.0; Found: C, 60.27; H,4.84; N, 12.88; C$_{21}$H$_{19}$ClN$_4$OS.½H$_2$O requires C, 60.06; H, 4.80; N, 13.34.

EXAMPLE 3

4-(8-Chloro-5,11-dihydro[1]benzoxepino[4,3-b]pyridin-11-ylidene)-N-cyano-N'-(4-pyridinylmethyl)-1-piperidine-carboximidamide

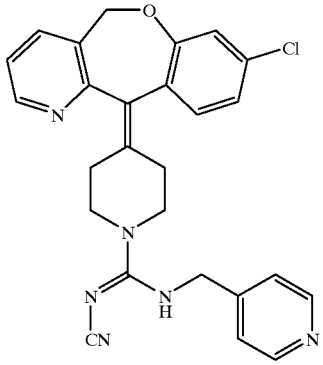

The product from Example 2 (1.2 g, 2.92 mmol) was stirred with 4-aminomethylpyridine (about 10 ml) at 100° C. for 1 hour. The reaction mixture was cooled and diluted with water (50 ml) and EtOAc (100 ml). The product crystallized and was allowed to stand overnight and then filtered off, washed with EtOAc (2×10 ml) and ether (2×50 ml); 1.2 g (96%), and dried: 4-(8-chloro-5,1 1-dihydro[1]benzoxepino[4,3-b]pyridin-11-ylidene)-N-cyano-N'-(4-pyridinylmethyl)-1-piperidine-carboximidamide; MS (CI, M+H)=471.

EXAMPLE 4

4-(3-Bromo-8-chloro-5,11-dihydro[1]benzoxepino[4,3-b]pyridin-11-ylidene)-1-(4-pyridine-acetyl)piperidine N1-oxide

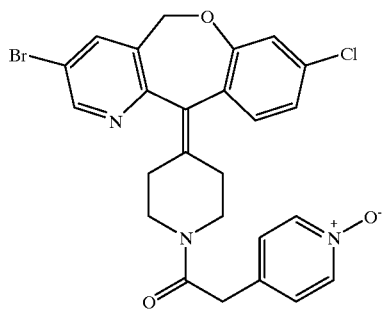

4-(3-Bromo-8-chloro-5,11-dihydro[1]benzoxepino[4,3-b]pyridin-11-ylidene)-piperidine (270 mg, 0.68 mmol), 4-pyridine-acetic acid 1-oxide (260 mg, 1.69 mmol), HOBT (200 mg, 1.48 mmol), and EDCl (320 mg, 1.67 mmol) were mixed and stirred at 0° C. in DMF (10 ml, anhydrous). NMM (0.5 ml, 4.53 mmol) was added, and the reaction mixture was stirred 2 hours at 0° C. and then overnight at 20° C. The solvent was evaporated off, water (20 ml) was added, and the mixture was extracted with methylene chloride (3×50 ml) and the extract was dried (MgSO$_4$), filtered and evaporated, yielding a crude product which was chromatographed on silica gel and eluted with 12%ethylacetate/hexanes containing 2% ammonium hydroxide. The product was recrystallized from ether to afford a white powder, 4-(3-bromo-8-chloro-5,11-dihydro[1]benz-oxepino[4,3-b]pyridin-11-ylidene)-1-(4-pyridine-acetyl)piperidine N1-oxide (260 mg, 72%); MS (FAB, M+H)=526.

EXAMPLE 5

4-(8-Chloro-5,11-dihydro[1]benz-oxepino[4,3-b]pyridin-11-ylidene)-1-(4-pyridine-acetyl)piperidine

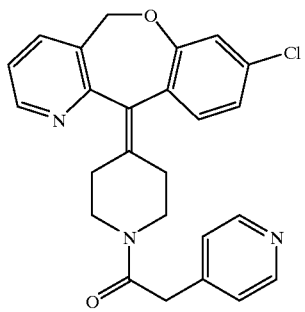

The title compound was prepared according to the method of Example 4 from 4-(8-chloro-5,11-dihydro[1]benzoxepino[4,3-b]pyridin-11-ylidene)-piperidine, 4-pyridine-acetic acid hydrochloride, HOBT, EDCl and NMM in DMF. 4-(8-Chloro-5,11-dihydro[1]benz-oxepino[4,3-b]pyridin-11-ylidene)-1-(4-pyridine-acetyl)piperidine was obtained as a white foam; MS (CI, M+H)=432; anal.: found: C, 68.71; H, 5.44; N, 9.44; $C_{25}H_{22}ClN_3O_2$ requires: C, 69.52; H, 5.13; N, 9.73.

EXAMPLE 6

4-(8-Chloro-5,11-dihydro[1]benz-oxepino[4,3-b]pyridin-11-ylidene)-1-(3-pyridine-acetyl)piperidine

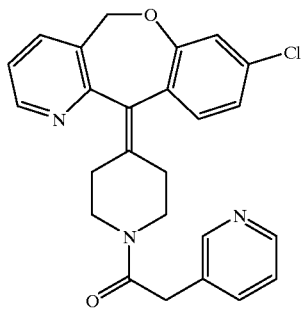

The title compound was prepared according to the method of Example 4 from 4-(8-chloro-5,11-dihydro[1]benzoxepino[4,3-b]pyridin-11-ylidene)-piperidine, 3-pyridine-acetic acid hydrochloride, HOBT, EDCl and NMM in DMF. 4-(8-Chloro-5,11-dihydro[1]benz-oxepino[4,3-b]pyridin-11-ylidene)-1-(3-pyridine-acetyl)piperidine was obtained as a white foam; MS (CI, M+H)=432; anal.: found: C, 68.85; H, 5.53; N, 9.49; $C_{25}H_{22}ClN_3O_2$ requires: C, 69.52; H,5.13; N,9.73.

EXAMPLE 7A 4-(9-Bromo-8-chloro-5,11-dihydro[1]benzoxepino[4,3-b]pyridin-11-ylidene)-1-(4-pyridine-acetyl)piperidine N1-oxide

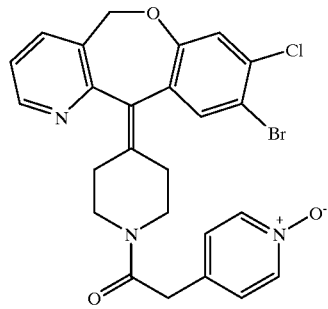

4-(9-Bromo-8-chloro-5,11-dihydro[1]benzoxepino[4,3-b]pyridin-11-ylidene)-piperidine (130 mg, 0.33 mmol), 4-pyridine-acetic acid 1-oxide (130 mg, 0.85 mmol), HOBT (120 mg, 0.89 mmol), and EDCl (160 mg, 0.83 mmol) were stirred at 0° C. in DMF (5 ml, anhydrous). N-Methylmorpholine (0.5 ml, 4.53 mmol) was added, and the reaction mixture was stirred overnight at 20° C. The solvent was evaporated off, and the residue was extracted with methylene chloride (2×100 ml) and water (30 ml). The organic layer was separated and dried ($MgSO_4$), filtered and evaporated, yielding an oil which was chromatographed on silica gel and eluted with 15%methanol/ethylacetate containing 2% ammonium hydroxide. The product was obtained as a white solid, 4-(9-bromo-8-chloro-5,11-dihydro[1]benzoxepino[4,3-b]pyridin-11-ylidene)-1-(4-pyridine-acetyl)piperidine N1-oxide (170 mg, 98%). MS (FAB, M+H)=526.

EXAMPLE 7B 4-(8-Chloro-5,11-dihydro[1]benzoxepino[4,3-b]pyridin-11-ylidene)-1-(4-pyridine-acetyl)piperidine N1-oxide

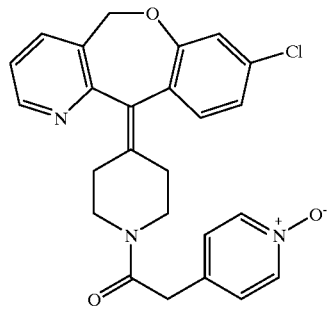

4-(8-Chloro-5,11-dihydro[1]benzoxepino[4,3-b]pyridin-11-ylidene)-1 -(4-pyridine-acetyl)piperidine N1-oxide was prepared similarly from 4-(8-chloro-5,11-dihydro[1]benzoxepino[4,3-b]pyridin-11-ylidene)-piperidine and 4-pyridine-acetic acid 1-oxide.

EXAMPLE 8

4-(8-Chloro-5,11-dihydro-[1]benzothiepino[4,3-b]pyridin-11-yl)-1-(4-pyridinyl-acetyl)piperazine

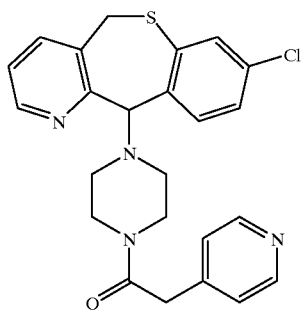

DEC (464 mg, 2.42 mmol), HOBT (327 mg, 2.42 mmol), and 4-pyridine-acetic acid (332 mg, 2.42 mmol) were added to 1-(8-chloro-5,11-dihydro-[1]benzothiepino[4,3-b]pyridin-11-yl)-piperazine (400 mg, 1.21 mmol) and NMM (5.3 ml) in DMF (8 ml), and the mixture was stirred at room temperature for 19 hours. Water (30 ml) and EtOAc (50 ml) were added, and the layers were mixed and separated. The aqueous layer was extracted with EtOAc (3×40 ml). The aqueous layer was basified with saturated NaHCO$_3$ and was extracted with CH$_2$Cl$_2$ (2×20 ml). The organic layers were combined, washed with brine, dried (Na$_2$SO$_4$), decanted and concentrated; the crude product (659 mg) was purified by flash chromatography (30%acetone/CH$_2$Cl$_2$ to 5%MeOH/CH$_2$Cl$_2$) and obtained as a white solid (344 mg, 63%); MS (FAB, M+H)=451; HRMS: calc.: 451.1359; found: 451.1355.

EXAMPLE 9A 4-(8-Chloro-5,11-dihydro-[1]benzothiepino[4,3-b]pyridin-11-yl)-1-(4-pyridine-acetyl)piperazine N1-oxide

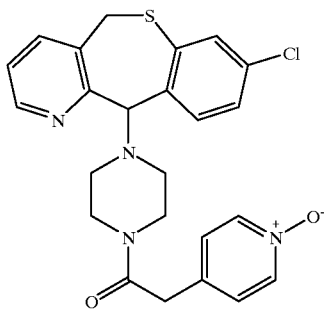

The title compound (531 mg, 93%) was prepared similarly from 1-(8-chloro-5,11-dihydro-[1]benzothiepino[4,3-b]pyridin-11-yl)-piperazine (400 mg, 1.21 mmol) and 4-pyridine-acetic acid 1-oxide (371 mg, 2.42 mmol); MS (FAB, M+H)=467.1; HRMS: calc.: 467.1309; found: 467.1300.

EXAMPLE 9B 4-(8-Chloro-5,11-dihydro-[1]benzothiepino[4,3-b]pyridin-11-ylidene)-1-(4-pyridine-acetyl)piperidine N1-oxide

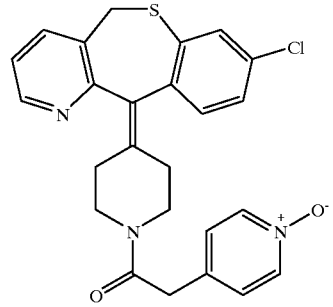

The title compound (369 mg, 95%) was prepared similarly from 1-(8-chloro-5,11-dihydro-[1]benzothiepino[4,3-b]pyridin-11-ylidene)-piperidine (275 mg) and 4-pyridine-acetic acid 1-oxide (25 mg); HRMS: calc.: 464.1200; found: 464.1193.

EXAMPLE 10

4-(8-Chloro-5,11-dihydro-[1]benzothiepino[4,3-b]pyridin-11-yl)-1-(1-methyl-4-piperidine-acetyl)piperazine

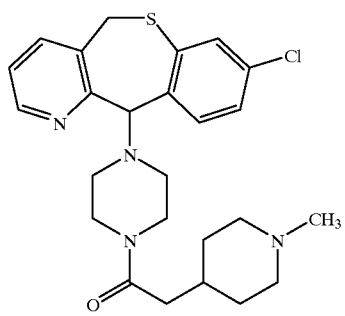

The title compound (547 mg, 96%) was prepared similarly from (8-chloro-5,11-dihydro-[1]benzothiepino[4,3-b]pyridin-11-yl)-piperazine (400 mg, 1.21 mmol) and 1-methyl-4-piperidine-acetic acid (380 mg, 2.42 mmol); found: Cl, 7.73; C$_{25}$H$_{31}$ClN$_4$OS requires: Cl, 7.53; MS (FAB, M+H)=471.1.

EXAMPLE 11A 1,1-Dimethylethyl 4-[2-[4-(8-chloro-5,11-dihydro-[1]benzothiepino[4,3-b]pyridin-11-yl)-1-piperazinyl]2-oxoethyl]-1-piperidinecarboxylate

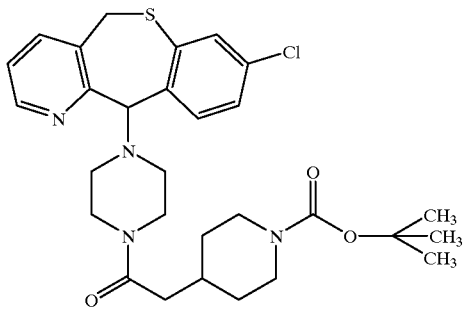

The title compound (563 mg) was prepared similarly from 1-(8-chloro-5,11-dihydro-[1]benzothiepino[4,3-b]pyridin-11-yl)-piperazine (400 mg, 1.21 mmol) and 1-(1,1-dimethylethoxycarbonyl)-4-piperidine-acetic acid (589 mg, 2.42 mmol); MS (CI, M+H)=557; HRMS: calc.: 557.2353; found: 557.2351.

EXAMPLE 11B 1,1-Dimethylethyl 4-[2-[4-(8-chloro-5,11-dihydro-[1]benzothiepino[4,3-b]pyridin-11-ylidene)-1-piperidinyl]2-oxoethyl]-1-piperidine-carboxylate

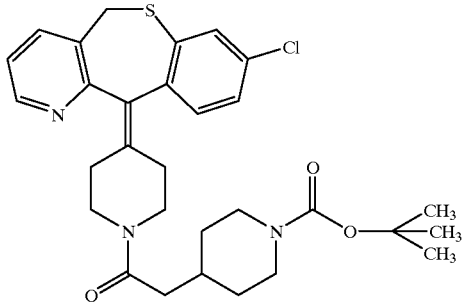

The title compound was prepared similarly from 1-(8-chloro-5,11-dihydro-[1]benzothiepino[4,3-b]pyridin-11-ylidene)-piperidine and 1-(1,1-dimethylethoxycarbonyl)-4-piperidine-acetic acid; HRMS: calc.: 554.2244; found: 554.2245.

EXAMPLE 12A 4-(8-Chloro-5,11-dihydro-[1]benzothiepino[4,3-b]pyridin-11-yl)-1-(4-piperidinyl-acetyl)piperazine

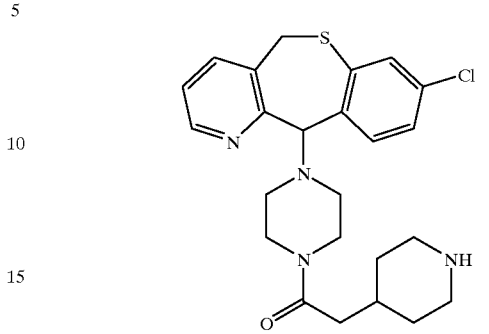

1,1-Dimethylethyl 4-[2-[4-(8-chloro-5,11-dihydro-[1]benzothiepino[4,3-5 b]pyridin-11-yl)-1-piperazinyl]2-oxoethyl]-1-piperidinecarboxylate (240 mg, 0.431 mmol) was combined with $CH_2Cl_2$ (2.5 ml) in a 10 ml flask, and the mixture was cooled to 0° C. Trifluoroacetic acid (TFA) (1.9 ml) was added through a syringe, and the reaction mixture was stirred at room temperature for 1.5 hours. The reaction was then quenched with the addition of 2.5 M NaOH to pH 12, and more water and $CH_2Cl_2$ were added. The layers were shaken and separated, and the aqueous layer was extracted with more $CH_2Cl_2$ (4×30 ml). The combined organic phases were washed with brine, dried ($Na_2SO_4$), decanted and concentrated. The crude residue (200 mg) was purified by flash chromatography (10%MeOH/$CH_2Cl_2$ to 10%MeOH/$CH_2Cl_2$/$NH_4OH$) and the pure product was obtained (186 mg), MS (FAB, M+H)=457.2.

EXAMPLE 12B 4-(8-Chloro-5,11-dihydro-[1]benzothiepino[4,3-b]pyridin-11-ylidene)-1-(4-pipeeridine-acetyl)piperidine

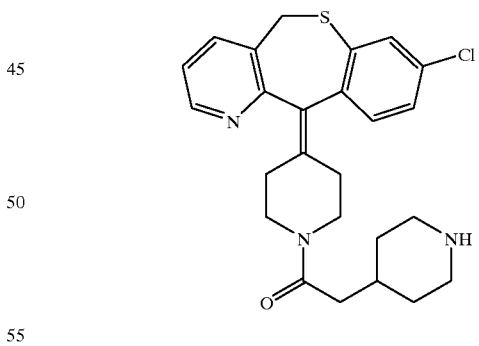

1,1-Dimethylethyl 4-[2-[4-(8-chloro-5,11-dihydro-[1]benzothiepino[4,3-b]pyridin-11-ylidene)-1-piperidinyl]2-oxoethyl]-1-piperidinecarboxylate (150 mg) in $CH_2Cl_2$ (10 ml) and trifluoroacetic acid (2 ml, in $CH_2Cl_2$, 10 ml) were mixed and allowed to stand at 0° C. After 30 minutes, the mixture was warmed to room temperature, and further trifluoroacetic acid (200 μl) was added. The mixture was left at room temperature for 30 minutes and evaporated to dryness, and the residue was dissolved in 5% NaOH and EtOAc (25 ml). The aqueous phase was washed with further EtOAc (3×25 ml); the organic phases were combined, washed with brine, dried (MgSO$_4$), filtered and concentrated to afford a viscous oil. This was triturated with hexane/acetone to afford an off-white foam, 92 mg (68%); HRMS: calc.: 454.1720; found: 454.1722.

EXAMPLE 13

4-(8-Chloro-5,11-dihydro-[1]benzothiepino[4,3-b]pyridin-11-yl)-1-[3-(2-nitro-phenyl)-2-oxopropanoyl]-4-piperidine-acetyl)piperazine

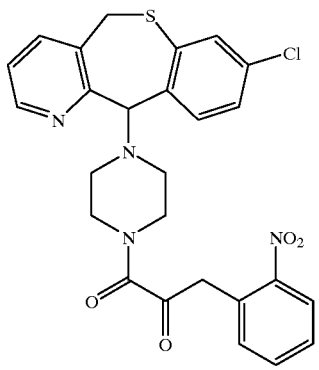

The title compound (66%) [m.p. 104–108° C., MS: FAB, M+H=523] was prepared similarly from 1-(8-chloro-5,11-dihydro-[1]benzothiepino[4,3-b]pyridin-11-yl)-piperazine (400 mg, 1.21 mmol) and 3-(2-nitrophenyl)-2-oxopropanoic acid (506 mg, 2.42 mmol); found: C, 59.57; H, 4.78; N, 10.37; Cl, 6.75; C$_{26}$H$_{23}$ClN$_4$O$_4$S requires: C, 59.71; H, 4.43; N, 10.71; Cl, 6.78; MS (FAB, M+H)=523.

EXAMPLE 14A 4-(8-Chloro-5,11-dihydro-[1]benzothiepino[4,3-b]pyridin-11-yl)-1-[(4-pyridinyl-thio)acetyl]piperazine

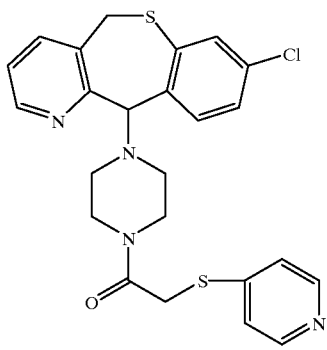

The title compound (548 mg, 94%) [MS (FAB, M+H)=483.1] was prepared similarly from 1-(8-chloro-5,11-dihydro-[1]benzothiepino[4,3-b]pyridin-11-yl)-piperazine (400 mg, 1.21 mmol) and (4-pyridinylthio)acetic acid (410 mg, 2.42 mmol).

EXAMPLE 14B 4-(8-Chloro-5,11-dihydro-[1]benzothiepino[4,3-b]pyridin-11-ylidene)-1-[(4-pyridinylthio)acetyl]piperidine

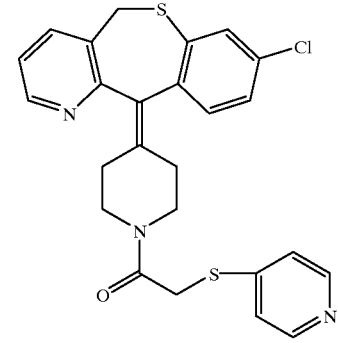

The title compound (548 mg, 94%) [MS: FAB, M+H=483.1] was prepared by the method of Example 4 from 1-(8-chloro-5,11-dihydro-[1]benzothiepino[4,3-b]pyridin-11-ylidene)-piperidine (200 mg) and (4-pyridinylthio)acetic acid (200 mg), except that the reaction was allowed to proceed for 28 hours and the chromatography was carried out in 3%MeOH/CH$_2$Cl$_2$, increasing to 5%MeOH/CH$_2$Cl$_2$; 287 mg product (96%).

EXAMPLE 15A

4-[2-[4-(8-Chloro-5,11-dihydro-[1]benzothiepino[4,3-b]pyridin-11-yl)-1-piperazinyl]-2-oxoethyl]-1-piperidinecarboxamide

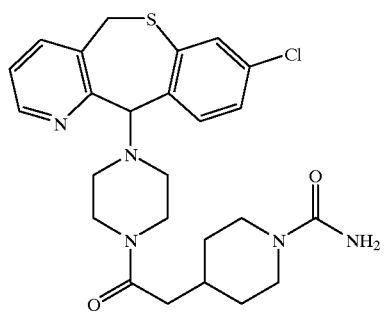

4-(8-Chloro-5,11-dihydro-[1]benzothiepino[4,3-b]pyridin-11-yl)-1-(4-piperidine-acetyl)piperazine (270 mg, 0.591 mmol) was added to anhydrous CH$_2$Cl$_2$ (2.7 ml). TMSNCO (320 mg, 0.37 ml, 2.36 mmol) was added by syringe. The mixture was stirred at room temperature for 90 hours and then quenched with saturated NaHCO$_3$. More water and CH$_2$Cl$_2$ were added, and the mixture was shaken and separated. The aqueous phase was extracted with CH$_2$Cl$_2$ (4×20 ml), and the combined organic phases were washed with brine, dried (Na$_2$SO$_4$), decanted and concentrated. The crude residue was purified by flash chromatography (5%MeOH/CH$_2$Cl$_2$ to 10%MeOH/CH$_2$Cl$_2$/NH$_4$OH) and the pure product was obtained (295 mg, 66%) MS (FAB, M+H)=529.

EXAMPLE 15B

4-[2-[4-(8-Chloro-5,11-dihydro-[1]benzothiepino[4,3-b]pyridin-11-ylidene)-1-piperidinyl]-2-oxoethyl]-1-piperidinecarboxamide

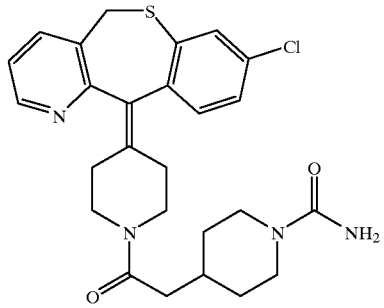

The title compound was prepared by a similar procedure from 4-[2-[4-(8-chloro-5,11-dihydro-[1]benzothiepino[4,3-b]pyridin-11-ylidene)-1-piperidinyl]-2-oxoethyl]-piperidine (120 mg, 0.265 mmol) in $CH_2Cl_2$ (3 ml), to which TMSNCO (200 μl, 170 mmol) was added at 0° C. After 5 minutes at 0° C., the mixture was stirred 3.5 hours at room temperature. The reaction mixture was diluted with water and extracted with $CH_2Cl_2$; the organic phase was washed with $NaHCO_3$ solution and brine, dried over $MgSO_4$, filtered and concentrated. The product was chromatographed on silica in 5%MeOH/$CH_2Cl_2$ and eluted with 10%MeOH/$CH_2Cl_2$ to afford a white solid (103 mg); HRMS: calc.: 497.1778; found: 497.1766.

EXAMPLE 16A 4-(8-Chloro-5,11-dihydro-[1]benzothiepino[4,3-b]pyridin-11-yl)-1-(4-pyridine-acetyl)piperazine 6,6-dioxide

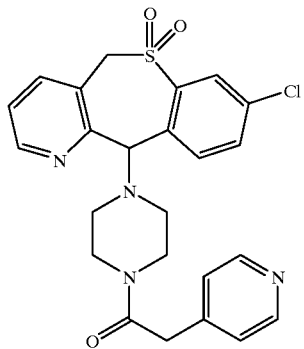

1-(8-Chloro-5,11-dihydro-[1]benzothiepino[4,3-b]pyridin-11-yl)-4-(4-pyridine-acetyl)piperazine (300 mg, 0.665 mmol) and methanesulfonic acid (5.46 ml of a 0.5 N solution in $CH_2Cl_2$) were stirred at room temperature for 15 minutes. 3-Chloroperbenzoic acid (431 mg, 2.0 mmol) was added, and the mixture was stirred at room temperature for two hours. The reaction was quenched with 2.5 M NaOH to pH 12 and shaken with $CH_2Cl_2$. The layers were separated and the aqueous layer was extracted with more $CH_2Cl_2$ (5×20 ml). The combined organic phases were washed with brine, dried ($Na_2SO_4$), decanted and concentrated. The crude residue (318 mg) was purified by flash chromatography (20%acetone/$CH_2Cl_2$ to 50%acetone/$CH_2Cl_2$ to 5%MeOH/$CH_2Cl_2$) and three fractions (60 mg, 68 mg, and 54 mg) were obtained. TLC suggested that the first two were the desired product; these were combined and chromatographed to afford the pure product (81 mg); MS (CI, M+H)=483.

EXAMPLE 16B 4-(8-Chloro-5,11-dihydro-[1]benzothiepino[4,3-b]pyridin-11-ylidene)-1-(4-pyridine-acetyl)piperidine 6,6-dioxide

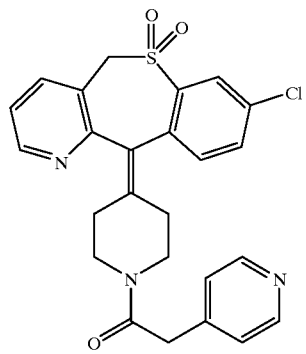

The title compound was prepared similarly from 4-(8-chloro-5,11-dihydro-[1]benzothiepino[4,3-b]pyridin-11-ylidene)-1-(4-pyridine-acetyl)piperidine (45 mg) and 3-chloroperbenzoic acid (55 mg), except that the reaction temperature was raised to 25° C. after 30 minutes and a second portion (30 mg) of 3-chloro-perbenzoic acid was added after 1 hour at 25° C. Yield: 59 mg; the product showed a strong band at 1320 $cm^{-1}$ due to $SO_2$; MS (CI, M+H)=480.0.

EXAMPLE 17A 4-(8-Chloro-5,11-dihydro-[1]benzothiepino[4,3-b]pyridin-11-yl)-1-(4-pyridine-acetyl)piperazine N1, 6,-dioxide [sulfoxide] and the corresponding N1,6,6-trioxide [sulfone]

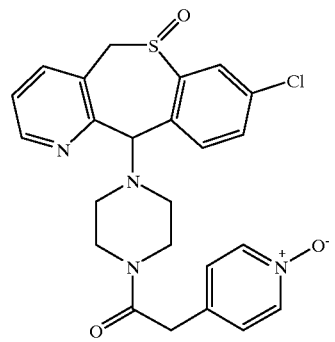

and

-continued

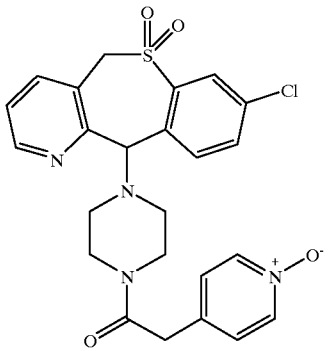

4-(8-Chloro-5,11-dihydro-[1]benzothiepino[4,3-b]pyridin-11-yl)-1-(4-pyridine-acetyl)piperazine N1-oxide (300 mg, 0.642 mmol) in CH$_2$Cl$_2$ (5 ml) was cooled to 0° C., and methanesulfonic acid (10.28 ml of a 0.5 N solution in CH$_2$Cl$_2$, 5.14 mmol) was added. The mixture was stirred at 0° C. for 20 minutes. 3-Chloroperbenzoic acid (313 mg, 1.45 mmol) was added and the mixture was stirred for 35 minutes. The reaction was quenched by the addition of 2.5 M NaOH to pH 14. Water and CH$_2$Cl$_2$ were added, and the layers were separated. The aqueous layer was extracted three times more with CH$_2$Cl$_2$; the combined organic phases were washed with brine, dried (Na$_2$SO$_4$), decanted and concentrated to a mixture of sulfoxide and sulfone. This mixture (365 mg) was subjected to flash chromatography on silica, and afforded two fractions, the sulfone (65 mg, 20%) and the sulfoxide (133 mg, 43%); MS of sulfone: FAB (M+H)=499.2; MS of sulfoxide: FAB (M+H)=483.2.

EXAMPLE 17B 4-(8-Chloro-5,11-dihydro-[1]benzothiepinof4,3-b]pyridin-11-yl)-1-(4-pyridine-acetyl)piperazine N1,6,6-trioxide

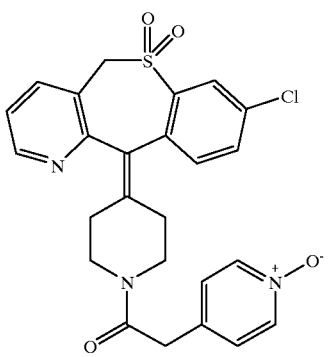

The title compound was prepared similarly from 4-(8-chloro-5,11-dihydro-[1]benzothiepino[4,3-b]pyridin-11-yl)-1-(4-pyridine-acetyl)piperazine N1-oxide (60 mg) and 3-chloroperbenzoic acid (98 mg), and was obtained in 65% yield, 42 mg; MS (CI, M+H)=469.

EXAMPLE 18

Methyl 4-(8-chloro-5,11-dihydro-[1]benzothiepino[4,3-b]pyridin-11-yl)-N-cyano-1-piperazinecarboximidothioate

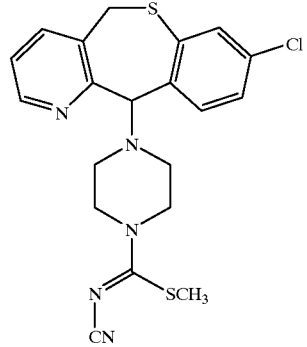

1-(8-Chloro-5,11-dihydro-[1]benzothiepino[4,3-b]pyridin-11-yl)-piperazine (400 mg, 1.21 mmol) was combined with ETOH (6 ml) in a 25 ml flask, and dimethyl N-cyanodithio-iminocarbonate (90%, 216 mg, 1.33 mmol) was added. The reaction mixture was stirred under reflux overnight. Ethanol was distilled off from the reaction, and the resulting tar was purified by flash chromatography to afford 499 mg (96%) of the desired product: MS (FAB, M+H)=430.1.

EXAMPLE 19

4-(8-Chloro-5,11-dihydro[1]benzothiepino[4,3-b]pyridin-11-yl)-N-cyano-N'-(4-pyridinylmethyl)-1-piperazine-carboximidamide

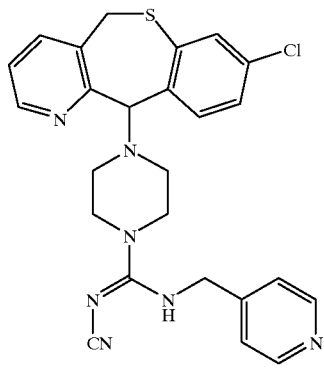

Methyl 4-(8-chloro-5,11-dihydro-[1]benzothiepino[4,3-b]pyridin-11-yl)-N-cyano-1-piperazinecarboximidothioate (200 mg, 0.465 mmol) was dissolved in acetonitrile (1 ml) in a 25 ml flask, and 4-aminomethylpyridine (0.94 ml, 9.30 mmol) was added. The mixture was refluxed for 1.6 hours. The reaction mixture was cooled and then acetonitrile was distilled off. The resulting tar was dissolved in water and CH$_2$Cl$_2$. The layers were separated; the aqueous layer was extracted three times with CH$_2$Cl$_2$. The combined organic layers were washed with brine, dried (MgSO$_4$), filtered through 'Celite' and concentrated. The residue was partially purified by flash chromatography, and the product (228 mg) was purified by further chromatography to afford the pure product (193 mg, 87%); MS (CI, M+H)=490.

EXAMPLE 20A

N-[(1,3-Benzodioxol-5-yl)methyl]-4-(8-chloro-5,11-dihydro[1]benzothiepino[4,3-b]pyridin-11-yl)-N'-cyano-1-piperazine-carboximidamide

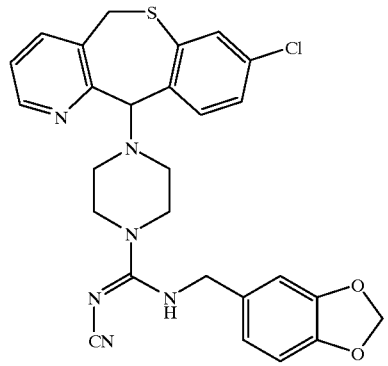

Methyl 4-(8-chloro-5,11-dihydro-[1]benzothiepino[4,3-b]pyridin-11-yl)-N-cyano-1-piperazine-carboximidothioate (184 mg, 0.428 mmol) was combined with 1,3-benzodioxol-5-ylmethylamine [piperonylamine] (1.07 ml, 8.56 mmol) in a 10 ml flask, and the mixture was stirred at 100° C. for three hours. The reaction mixture was cooled to room temperature and diluted with water and $CH_2Cl_2$. The layers were shaken together and separated, and the aqueous extract was extracted several times with $CH_2Cl_2$. The combined organic layers were washed with brine, dried ($MgSO_4$), filtered through 'Celite' and concentrated. The residue (over 2 g) was first filtered through a plug of silica gel and eluted with 15%acetone/$CH_2Cl_2$), and then further chromatographed more carefully and eluted with 2%EtOH/$CH_2Cl_2$, increasing gradually to 40%EtOH/$CH_2Cl_2$, to afford the pure product, 155 mg (68%); MS (FAB, M+H)= 533.6.

EXAMPLE 20B

N-[(1,3-Benzodioxol-5-yl)methyl]-4-(8-chloro-5,11-dihydro[1] benzothiepino[4,3-b]pyridin-11-yl)-N'-cyano-1-piperidine-carboximidamide

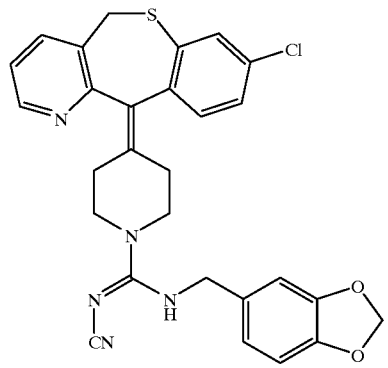

This compound could be prepared similarly from methyl 4-(8-chloro-5,11-dihydro-[1]benzothiepino[4,3-b]pyridin-11-yl)-N-cyano-1-piperidine-carboximidothioate and 1,3-benzodioxol-5-ylmethylamine.

EXAMPLE 21

4-(8-Chloro-5,11-dihydro[1]benzothiepino[4,3-b]pyridin-11-yl)-N-cyano-N'-(3-pyridinylmethyl)-1-piperazine-carboximidamide N1-oxide

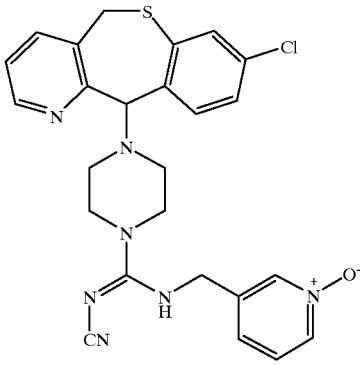

Methyl 4-(8-chloro-5,11-dihydro-[1]benzothiepino[4,3-b]pyridin-11-yl)-N-cyano-1-piperazine-carboximidothioate (275 mg, 0.640 mmol) was combined with acetonitrile (0.85 ml) and freshly dried 3-aminopyridine 1-oxide (1.00 g, 8.06 mmol). The mixture was refluxed for 5 hours and then evaporated to dryness. The residual tar was partitioned between water and $CH_2Cl_2$. The aqueous layer was extracted four further times with $CH_2Cl_2$. The combined organic layers were washed with brine, dried ($MgSO_4$), filtered through 'Celite' and concentrated. The crude product (348 mg) was purified by flash chromatography, and the product (272 mg) was confirmed by $^1$H-NMR; MS (FAB, M+H)= 506.2.

EXAMPLE 22

Methyl [4-(8-chloro-5,11-dihydro[1]benzothiepino[4,3-b]pyridin-11-ylidene)-N-cyano-1-piperidinecarboximidothioate

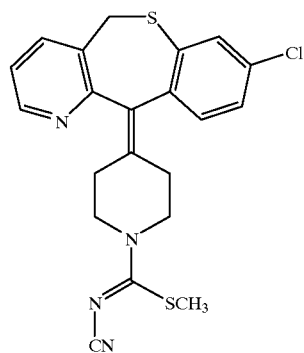

4-(8-Chloro-5,11-dihydro[1]benzothiepino[4,3-b]pyridin-11-ylidene)-piperidine (500 mg) was dissolved in $CH_3CN$ (8 ml) and $Et_3N$ (2 ml) at room temperature. $(MeS)_2C=NCN$ (280 mg) was added and the mixture was heated at 90° C. for 2.5 hours. The solvent was distilled off and the product was chromatographed on silica in $CH_2Cl_2$ and was eluted with 2%MeOH/$CH_2Cl_2$ and then with 5%MeOH/$CH_2Cl_2$, to afford 385 mg (59%) of a light tan solid, methyl [4-(8-chloro-5,11-dihydro[1]benzothiepino[4,3-b]pyridin-11-ylidene)-N-cyano-1-piperidinecarboximidothioate; MS (FAB, M+H)=427.

EXAMPLE 23

4-(8-Chloro-5,11-dihydro[1]benzothiepino[4,3-b]pyridin-11-ylidene)-N-cyano-N'-(4-pyridinylmethyl)-1-piperidine-carboximidamide

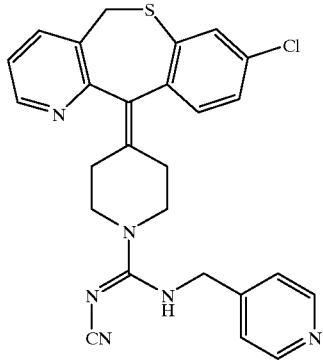

Methyl [4-(8-chloro-5,11-dihydro[1]benzothiepino[4,3-b]pyridin-11-5ylidene)-N-cyano-1-piperidinecarboximidothioate (250 mg, 0.59 mmol) was dissolved in $CH_3CN$ (2 ml) and 4-aminomethylpyridine (319 mg, 300 μl, 2.95 mmol) was added. The solution was heated at 100° C. for 4 hours, and then stirred at room temperature overnight. The product was chromatographed on silica to afford an orange-yellow solid, 238 mg (83%). A portion was decolorized with carbon (in acetone), filtered, and isolated as an off-white solid, 4-(8-chloro-5,11-dihydro[1]benzothiepino[4,3-b]pyridin-11-ylidene)-N-cyano-N'-(4-pyridinyl-methyl)-1-piperidine-carboximidamide, decomposing above ~150° C.; MS (FAB, M+H)=487.

EXAMPLE 24

4-(8-Chloro-5,11-dihydro[1]benzothiepino[4,3-b]pyridin-11-ylidene)-N-cyano-N'-(3-pyridinylmethyl)-1-piperidine-carboximidamide N1-oxide

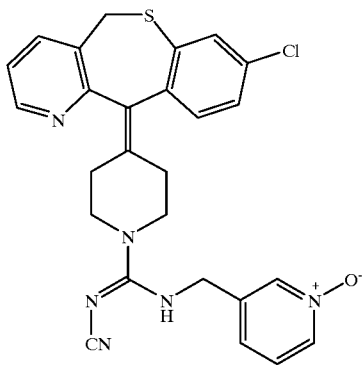

Methyl [4-(8-chloro-5,11-dihydro[1]benzothiepino[4,3-b]pyridin-11-ylidene)-N-cyano-1-piperidinecarboximidothioate (180 mg, 0.42 mmol) was dissolved in $CH_3CN$ (2 ml) and 3-aminomethylpyridine-1-oxide (190 mg) was added. The solution was heated at 80° C. for 48 hours. The reaction mixture was then cooled to room temperature and evaporated. The product was directly chromatographed on silica to afford the product, 84 mg (40%); found: C, 58.23; H, 4.91; N, 15.63; S, 6.29; calcd. for $C_{26}H_{23}ClN_6OS \cdot 2H_2O$: C, 57.93; H, 5.05; N, 15.59; S, 6.58; MS (FAB, M+H) =503.

EXAMPLE 25

4-(8-Chloro-5,11-dihydro[1]benzothiepino[4,3-b]pyridin-11-ylidene)-1-(pyridine-4-acetyl)-piperidine

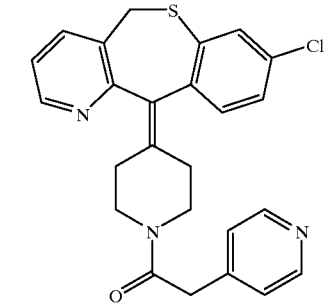

4-(8-Chloro-5,11-dihydro[1]benzothiepino[4,3-b]pyridin-11-ylidene)-piperidine (215 mg, 0.655 mmol), EDCl (250 mg), HOBT (180 mg), pyridine-4-acetic acid (180 mg), NMM (3 ml), and DMF (5 ml) were mixed at room temperature and stirred at room temperature for 24 hours. Water (50 ml) was added and the mixture was extracted with EtOAc (5×50 ml); the organic extract was washed with brine, dried ($MgSO_4$), filtered and concentrated; the product was chromatographed on silica gel in 5%MeOH/$CH_2Cl_2$ to afford 276 mg (94%) of an amorphous tan solid; MS (CI, M+H)=448.

EXAMPLE 26

4-(8-Chloro-5,11-dihydro[1]benzothiepino[4,3-b]pyridin-11-ylidene)-1-(1-methyl-4-piperidine-acetyl)-piperidine

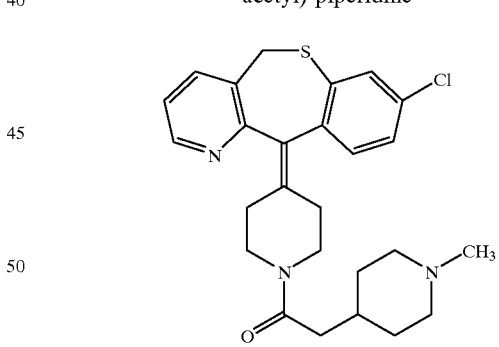

4-(8-Chloro-5,11-dihydro[1]benzothiepino[4,3-b]pyridin-11-ylidene)-piperidine (250 mg, 0.762 mmol), EDCl (290 mg), HOBT (200 mg), 1-methyl-4-piperidine-acetic acid (240 mg), NMM (3 ml), and DMF (5 ml) were mixed at room temperature and stirred at room temperature for 24 hours. Water (100 ml) was added and the mixture was extracted with EtOAc (5×75 ml); the aqueous emulsion forming after the second wash was washed with $CHCl_3$ (2×200 ml). The combined organic extracts were washed with brine, dried ($MgSO_4$), filtered and concentrated; the product was chromatographed on silica gel to afford 320 mg (90%) of an amorphous tan solid; MS (CI, M+H)=468.

EXAMPLE 27

1,1-Dimethylethyl 4-[2-[4-(8-chloro-5,11-dihydro-[1]benzothiepino[4,3-b]pyridin-11-yl)-1-piperazinyl]2-oxoethyl]-1-piperidinecarboxylate-6,6-dioxide

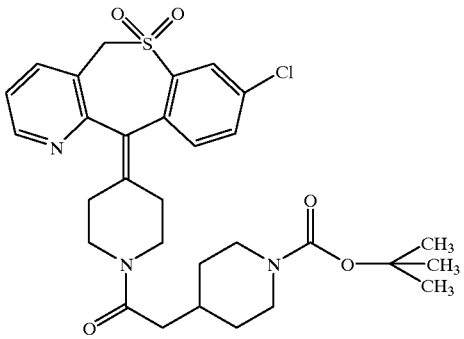

4-(8-Chloro-5,11-dihydro[1]benzothiepino[4,3-b]pyridin-11-ylidene)-piperidine (680 mg, 1.88 mmol), EDCl (540 mg), HOBT (390 mg), 1-(1,1-dimethylethoxycarbonyl)-4-piperidine-acetic acid (690 mg), NMM (5 ml), and DMF (12 ml) were mixed at room temperature and stirred at room temperature for 72 hours. The solvents were evaporated off, and the residue was diluted with water and NaHCO$_3$ solution, and the mixture was extracted with CH$_2$Cl$_2$. The combined organic extracts were washed with brine, dried (MgSO$_4$), filtered and concentrated; the product was chromatographed on silica gel to afford a viscous oil which contained DMF (by NMR). This residue was azeotroped with toluene to afford an amber solid, which was triturated with hexane to afford 880 mg (90%) of the desired product; MS (FAB, M+H)=586.

EXAMPLE 28

4-(8-Chloro-5,11-dihydro-[1]benzothiepino[4,3-b]pyridin-11-ylidene)-1-(4-piperidine-acetyl)piperidine-6,6-dioxide

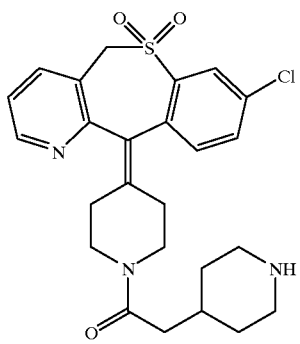

1,1-Dimethylethyl 4-[2-[4-(8-chloro-5,11-dihydro-[1]benzothiepino[4,3-b]pyridin-11-ylidene)-1-piperidinyl]2-oxoethyl]-1-piperidinecarboxylate-6,6-dioxide (850 mg, 1.45 mmol) was combined with CH$_2$Cl$_2$ (10 ml), and the mixture was cooled to 0° C. Trifluoroacetic acid (TFA) (5 ml) was added through a syringe, and the reaction mixture was stirred at 0° C. for 10 minutes and then at room temperature for 50 minutes. The reaction was then quenched with the addition of 5% NaOH and the mixture was extracted with CH$_2$Cl$_2$. The organic phases were washed with brine, dried (MgSO$_4$), filtered, and concentrated to afford the desired product: 591 mg (83%) after 16 hours' drying under vacuum; MS (CI, M+H)=486.

EXAMPLE 29

4-[2-[4-(8-Chloro-5,11-dihydro-[1]benzothiepino[4,3-b]pyridin-11-ylidene)-1-piperidinyl]-2-oxoethyl]-1-piperidinecarboxamide-6,6-dioxide

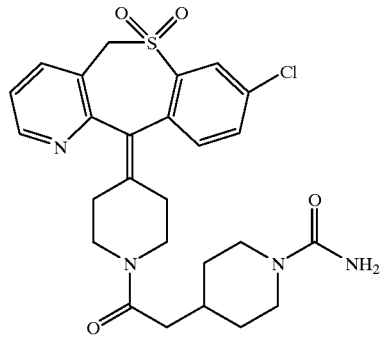

4-(8-Chloro-5,11-dihydro-[1]benzothiepino[4,3-b]pyridin-11-ylidene)-1-(4-piperidine-acetyl)piperidine-6,6-dioxide (300 mg, 0.62 mmol) was combined with CH$_2$Cl$_2$ (6 ml), and the mixture was cooled to 0° C. TMSNCO (700 μl) was added dropwise, and the reaction mixture was stirred at 0° C. for 10 minutes and then at room temperature for 5 hours. The reaction was then quenched by pouring into water and the mixture was extracted with CH$_2$Cl$_2$. The organic phases were washed with NaHCO$_3$ solution and brine, dried (MgSO$_4$), filtered, and concentrated. The residue was chromatographed on silica with 5%–10%MeOH/CH$_2$Cl$_2$ and then with 10%MeOH/CH$_2$Cl$_2$/1%NH$_4$OH to afford the pure product as a white solid (319 mg, 97%); MS (FAB, M+H)=529.

EXAMPLE 30

4-(8-Chloro-5,11-dihydro-5,5-dimethyl-[1]benzothiepino[4,3-b]pyridin-11-ylidene)-1-(4-pyridine-acetyl)piperidine-6,6-dioxide N1-oxide

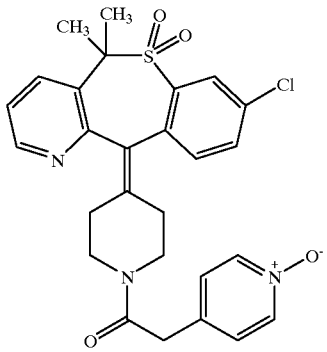

The title compound (110 mg) was prepared by the method of Example 4 from 4-(8-chloro-5,11-dihydro-5,5-dimethyl-[1]benzothiepino[4,3-b]pyridin-11-ylidene)-piperidine-6,6-dioxide (110 mg, 0.28 mmol) and 4-pyridine-acetic acid 1-oxide (85 mg); MS (FAB, M+H)=524.

EXAMPLE 31

4-(8-Chloro-5,11-dihydro-[1]benzothiepino[4,3-b]pyridin-11-yl)-1-(4-pyridine-acetyl)piperazine-6-oxide

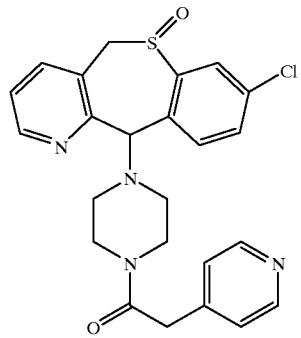

HOBT (155 mg, 1.15 mmol), DEC (220 mg, 1.15 mmol) and 4-pyridine-acetic acid (158 mg, 1.15 mmol) were added to 1-(8-chloro-5,11-dihydro-[1]benzothiepino[4,3-b]pyridin-11-yl)-piperazine 6-oxide (200 mg, 0.575 mmol) in NMM (2.6 ml) and DMF (4 ml). The reaction mixture was stirred at room temperature for 24 hours and then quenched with water and EtOAc. The layers were shaken and separated, and the aqueous layer was extracted with more EtOAc (2×20 ml) and then with $CH_2Cl_2$ (3×20 ml). The combined organic phases were washed with brine, dried ($Na_2SO_4$), decanted and concentrated. The crude residue was purified by flash chromatography (10%acetone/$CH_2Cl2$ to 5%MeOH/$CH_2Cl_2$ to 10%MeOH/$CH_2Cl_2$) and the pure product was obtained (231 mg); MS (FAB, M+H)=476.1.

EXAMPLE 32

4-[2-[4-(8-Chloro-5,11-dihydro-[1]benzothiepino[4,3-b]pyridin-11-yl)-1-piperazinyl]-2-oxoethyl]-1-piperidinecarboxamide 6-oxide

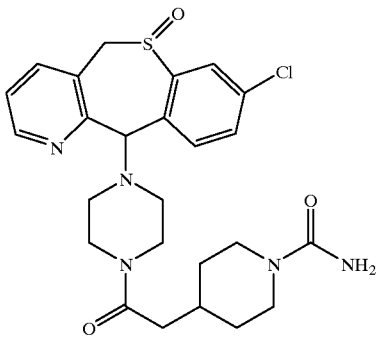

4-[2-[4-(8-Chloro-5,11-dihydro-[1]benzothiepino[4,3-b]pyridin-11-yl)-1-piperazinyl]-2-oxoethyl]-1-piperidinecarboxamide (200 mg, 0.400 mmol) was dissolved in HOAc (2.6 ml) at room temperature. $NaBO_3$ (88 mg, 0.88 mmol) was added, and the mixture was stirred at room temperature for 2.5 days. It was then basified to pH 14 with 2.5 M NaOH and extracted five times with $CHCl_3$. The combined organic layers were dried ($MgSO_4$), filtered through 'Celite' and concentrated. The residue (104 mg) was purified by flash chromatography (5%EtOH/$CH_2Cl_2$ to 10%EtOH/$CH_2Cl_2$), and the product (75 mg) was confirmed by $^1$H-NMR to be the sulfoxide; MS (FAB, M+H)=516.6.

EXAMPLE 33

3-[4-(8-Chloro-5,11-dihydro-[1]benzothiepino[4,3-b]pyridin-11-ylidene)-piperidin-1-yl]-3-(4'-fluorophenyl)-2-propene-nitrile

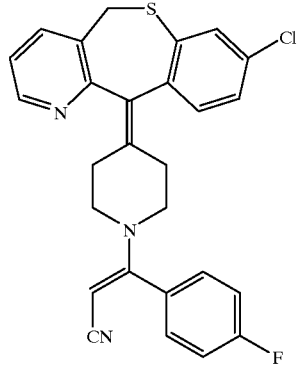

1-(8-Chloro-5,11-dihydro-[1]benzothiepino[4,3-b]pyridin-11-ylidene)-piperidine (200 mg, 0.61 mmol) was heated at 80° C. for 5 hours with 3-chloro-3-(4'-fluorophenyl)-2-propene-nitrile (310 mg) and di(2-propyl)amine (150 μl) in acetonitrile (5 ml), and then for 48 hours at 65–70° C. The solvent was evaporated off, and the residue was chromatographed directly on silica to afford the pure product as an off-white solid, 196 mg (68%); no m.p. but the compound becomes 'wet' or glassy and foams at ~125° C.; MS (FAB, M+H)=474.1.

EXAMPLE 34

1-(8-Chloro-6,11-dihydro-6-methyl-5H-pyrido[3,2-c][1]benzazepin-11-yl)-4-(4-pyridine-acetyl)piperazine N4-oxide

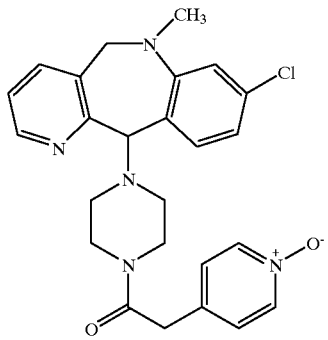

(8-Chloro-6,11-dihydro-6-methyl-5H-pyrido[3,2-c][1]benzazepin-11-yl)-piperazine (100 mg, 0.305 mmol), 4-pyridine-acetic acid 1-oxide (93.3 mg, 0.61 mmol), EDCl (0.116 g, 0.61 mmol) and HOBT (82.4 mg, 0.61 mmol) were dissolved in DMF (2 ml), and NMM (1 ml) was added. The reaction mixture was stirred at 20° C. for 18 hours and then diluted with water (50 ml), and the aqueous phase was then extracted with EtOAc (about 8 times) until no product was visible in the aqueous layer. The EtOAc phase was then washed with aqueous $Na_2CO_3$ and chromatographed on silica gel to afford the title compound (107 mg), m.p. 115–118° C.

EXAMPLE 35

4-(8-Chloro-6,11-dihydro-6-methyl-5H-pyrido[3,2-c][1]benzazepin-11-yl)-1-(4-pyridine-acetyl)piperazine

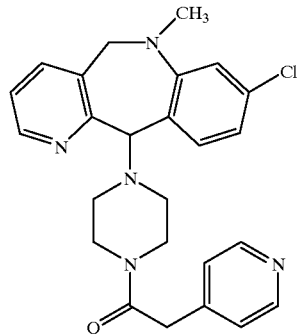

(8-Chloro-6,11-dihydro-6-methyl-5H-pyrido[3,2-c][1]benzazepin-11-yl)-piperazine (100 mg, 0.305 mmol), 4-pyridine-acetic acid (83.6 mg, 0.61 mmol), EDCl (0.116 g, 0.61 mmol) and HOBT (82.4 mg, 0.61 mmol) were dissolved in DMF (2 ml) and stirred for 1 minute, and then NMM (1 ml) was added. The reaction mixture was stirred at 20° C. for 21 hours and then diluted with water (50 ml), and the aqueous phase was then extracted with EtOAc (about 8 times) until no product was visible in the aqueous layer. The EtOAc phase was then washed with aqueous $Na_2CO_3$ and evaporated to a residue (152 mg). This was chromatographed on silica gel to afford partially purified title compound (123 mg), which was rechromatographed on silica gel; two fractions, 51.3 and 50.8 mg, were isolated. The latter gave m.p. 83–87° C.

EXAMPLE 36

Methyl 4-(8-chloro-6,11-dihydro-6-methyl-5H-pyrido[3,2-c][1]benzazepin-11-yl)-N-cyano-1-piperazinecarboximidothioate

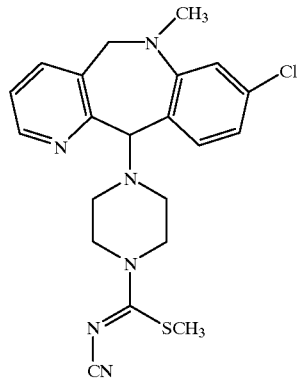

(8-Chloro-6,11-dihydro-6-methyl-5H-pyrido[3,2-c][1]benzazepin-11-yl)-piperazine (180 mg, 0.548 mmol) and $(MeS)_2C=NCN$ (88 mg, 90%, 0.55 mmol) were dissolved in ethanol (3 ml). The reaction mixture was refluxed for 2 hours and 45 minutes and then evaporated. The residue was chromatographed on silica gel to afford the title compound (111mg); HRMS: calcd. 427.1472; found 427.1465.

EXAMPLE 37

4-(8-Chloro-6,11-dihydro-6-methyl-5H-pyrido[3,2-c][1]benzazepin-11-yl)-N-cyano-N'-(4-pyridinylmethyl)-1-piperazine-carboximidamide

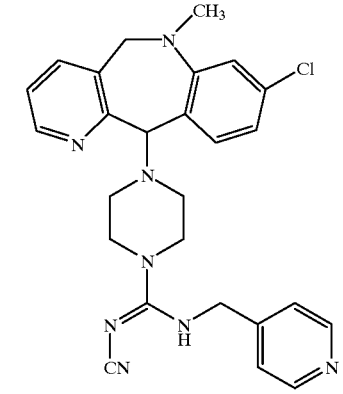

Methyl 4-(8-chloro-6,11-dihydro-6-methyl-5H-pyrido[3,2-c][1]benzazepin-11-yl)-N-cyano-1-piperazinecarboximidothioate (105 mg) and 4-aminomethyl-pyridine (0.45 ml) were heated at 80° C. in a sealed vial allowing escape of gases. Ice-water was then added, and the resulting tan solid was chromatographed on silica gel to afford the desired product, 107 mg; HRMS, FAB: calcd. 487.2125; found 487.2141.

EXAMPLE 38

1,1-Dimethylethyl 4-[2-[4-(8-chloro-6,11-dihydro-6-methyl-5H-pyrido[3,2-c][1]benzazepin-11-yl)-1-piperazinyl]2-oxoethyl]-1-piperidine-carboxylate

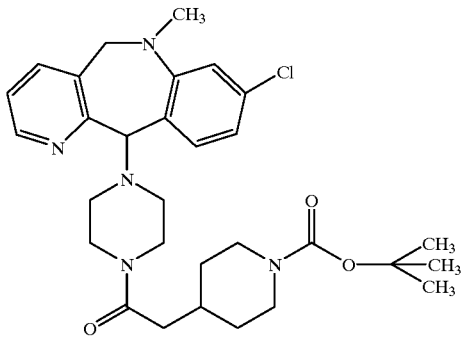

(8-Chloro-6,11-dihydro-6-methyl-5H-pyrido[3,2-c][1]benzazepin-11-yl)-piperazine (531 mg, 1.14 mmol), 1-(1,1-dimethylethoxycarbonyl)-4-piperidine-acetic acid (570 mg, 2.3 mmol), EDCl (439 mg) and HOBT (311mg) were dissolved in DMF (8 ml), and NMM (4 ml) was added. The reaction mixture was stirred at 20° C. for 20 hours and then water (100 ml) was added, and the resulting tan suspension was extracted with EtOAc (2×30 ml). The EtOAc phase was then washed with $Na_2CO_3$ (30 ml), dried over $Na_2SO_4$, filtered, and evaporated. The product was chromatographed over silica gel in $CH_2Cl_2$, and the column was eluted with $CH_2Cl_2$ and with $CH_2Cl_2$/MeOH (95:5). The resulting purer material (0.75 g) was rechromatographed over silica gel in hexane/acetone (85:15) and eluted with increasing amounts of acetone (finally 30%). The product was rechromatographed on silica gel to afford the title compound (0.19 g), m.p. 86–98° C.; found: C, 64.64; H, 7.39; N, 12.12; calcd. for $C_{30}H_{40}ClN_5O_3$: C, 65.03; H, 7.28; N, 12.64; HRMS: calcd. 554.2898; found 554.2891.

EXAMPLE 39

4-(8-Chloro-6,11-dihydro-6-methyl-5H-pyrido[3,2-c][1]benzazepin-11-yl)-1-(4-piperidine-acetyl)piperazine

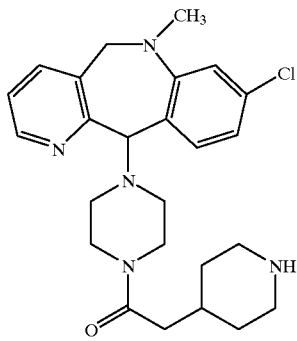

1,1-Dimethylethyl 4-[2-[4-(8-chloro-6, 11-dihydro-6-methyl-5H-pyrido[3,2-c][1]benzazepin-11-yl)-1-piperazinyl]2-oxoethyl]-1-piperidinecarboxylate (100 mg) was heated neat in vacuo at 180° C. for 10 hours. The product was chromatographed on silica gel. Five fractions, 5.4, 28,16.6, 16.7 and 10 mg, were obtained. The fifth fraction was shown to be the desired product, 85% pure by TLC; HRMS: calcd., 454.2374; found 454.2389.

ASSAYS

The compounds of the invention can be tested by standard methods, for example by those published in published PCT application WO 95/10514 published Apr. 20, 1995 (starting at page 61), the disclosure of which is hereby incorporated herein by reference. Particularly relevant assays and studies include In vitro enzyme assays, Cell-Based Assays, Cell Mat Assays, and In Vivo Anti-Tumor Studies.

Such Assays and Studies indicate that compounds of the Formula I above are selective inhibitors of Ras-FPT and can be used as anti-tumor agents. The following Table presents $IC_{50}$ values obtained in the test for Inhibition of farnesyl protein transferase, reported in published PCT application WO 95/10514. Percent inhibition was calculated relative to the DMSO vehicle control, and an $IC_{50}$ value was estimated.

TABLE OF COMPOUNDS PREPARED AND ACTIVITIES

| Ex. No. | $X^1$ | $X^2$ | $R^1,R^2$ | Y | A= | R | $IC_{50}$ ($\mu$m) |
|---|---|---|---|---|---|---|---|
| 1 | H | 8-Cl | H,H | O | N— | 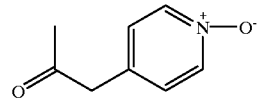 | 1.28 |
| 5 | H | 8-Cl | H,H | O | C= | 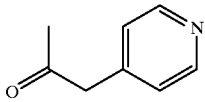 | 0.76 |
| 6 | H | 8-Cl | H,H | O | C= | 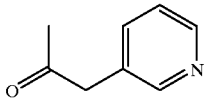 | 2.3 |
| 7B | H | 8-Cl | H,H | O | C= | 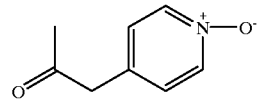 | 1.52 |
| 4 | 3-Br | 8-Cl | H,H | O | C= | 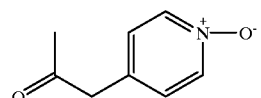 | 0.11 |
| 7A | H | 8-Cl, 9-Br | H,H | O | C= | 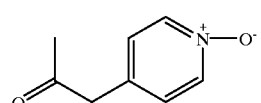 | >0.4 |
| 2 | H | 8-Cl | H,H | O | C= | —C(SCH$_3$)=N—CN | >0.14 |

-continued

TABLE OF COMPOUNDS PREPARED AND ACTIVITIES

| Ex. No. | X$^1$ | X$^2$ | R$^1$,R$^2$ | Y | A---- | R | IC$_{50}$ ($\mu$m) |
|---|---|---|---|---|---|---|---|
| 3 | H | 8-Cl | H,H | O | C= | -C(-NH-CH$_2$-4-pyridyl)=N-CN (acetimidate with N-CN, NH-CH$_2$-pyridyl) | >0.042 |
| 8 | H | 8-Cl | H,H | S | N— | -CH$_2$C(O)CH$_2$-(4-pyridyl) | 0.32 |
| 11A | H | 8-Cl | H,H | S | N— | -CH$_2$C(O)CH$_2$-(1-Boc-piperidin-4-yl) | >1.1 |
| 10 | H | 8-Cl | H,H | S | N— | -CH$_2$C(O)CH$_2$-(1-methylpiperidin-4-yl) | 2.1 |
| 13 | H | 8-Cl | H,H | S | N— | -CH$_2$C(O)C(O)CH$_2$-(2-nitrophenyl) | 3.8 |
| 14A | H | 8-Cl | H,H | S | N— | -CH$_2$C(O)CH$_2$-S-(4-pyridyl) | 1.0 |
| 9A | H | 8-Cl | H,H | S | N— | -CH$_2$C(O)CH$_2$-(4-pyridyl N-oxide) | 0.79 |
| 15A | H | 8-Cl | H,H | S | N— | -CH$_2$C(O)CH$_2$-(1-carbamoylpiperidin-4-yl) | 1.12 |
| 31 | H | 8-Cl | H,H | S=O | N— | -CH$_2$C(O)CH$_2$-(4-pyridyl) | 5 |
| 16A | H | 8-Cl | H,H | SO$_2$ | N— | -CH$_2$C(O)CH$_2$-(4-pyridyl) | 1.0 |
| 12A | H | 8-Cl | H,H | S | N— | -CH$_2$C(O)CH$_2$-(piperidin-4-yl) | 1.1 |
| 18 | H | 8-Cl | H,H | S | N— | —C(SCH$_3$)=N—CN | 0.30 |

-continued
TABLE OF COMPOUNDS PREPARED AND ACTIVITIES
| Ex. No. | X¹ | X² | R¹,R² | Y | A⁻⁻⁻⁻ | R | IC₅₀ (μm) |
|---|---|---|---|---|---|---|---|
| 19 | H | 8-Cl | H,H | S | N— | 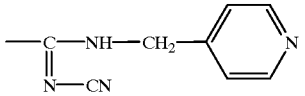 | 0.061 |
| 17A (sulfone) | H | 8-Cl | H,H | SO₂ | N— | 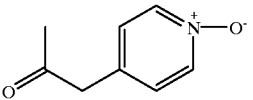 | 3.4 |
| 17A (sulfoxide) | H | 8-Cl | H,H | S=O | N— | 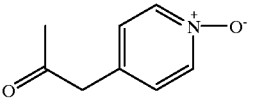 | >4.0 |
| 20A | H | 8-Cl | H,H | S | N— | 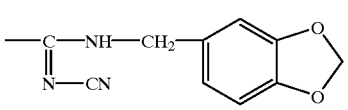 | >0.37 |
| 32 | H | 8-Cl | H,H | S=O | N— | 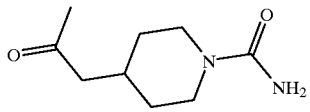 | >0.38 |
| 21 | H | 8-Cl | H,H | S | N— | 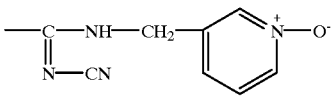 | 0.14 |
| 25 | H | 8-Cl | H,H | S | C= | 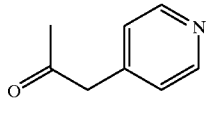 | 0.19 |
| 9B | H | 8-Cl | H,H | S | C= | 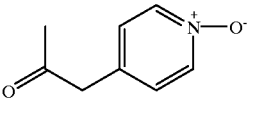 | 0.52 |
| 26 | H | 8-Cl | H,H | S | C= | 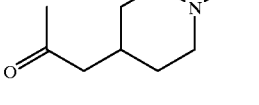 | 1.79 |
| 11B | H | 8-Cl | H,H | S | C= | 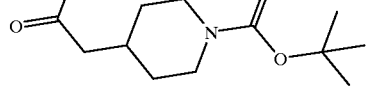 | 3.2 |
| 16B | H | 8-Cl | H,H | SO₂ | C= | 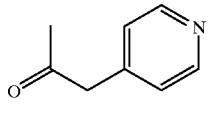 | 0.56 |

-continued

TABLE OF COMPOUNDS PREPARED AND ACTIVITIES

| Ex. No. | X$^1$ | X$^2$ | R$^1$,R$^2$ | Y | A---- | R | IC$_{50}$ ($\mu$m) |
|---|---|---|---|---|---|---|---|
| 15B | H | 8-Cl | H,H | S | C= | *piperidine with C(=O)NH$_2$ and acetyl group* | 0.92 |
| 17B | H | 8-Cl | H,H | SO$_2$ | C= | *pyridine N-oxide with acetyl linker* | >1.2 |
| 14B | H | 8-Cl | H,H | S | C= | *4-pyridyl-S-CH$_2$-C(=O)-* | 0.62 |
| 23 | H | 8-Cl | H,H | S | C= | —C(=N—CN)—NH—CH$_2$—(4-pyridyl) | 0.043 |
| 22 | H | 8-Cl | H,H | S | C= | —C(SCH$_3$)=N—CN | 0.20 |
| 12B | H | 8-Cl | H,H | S | C= | *4-piperidinyl-CH$_2$-C(=O)-* | 0.59 |
| 20B | H | 8-Cl | H,H | S | C= | —C(=N—CN)—NH—CH$_2$—(benzodioxole) | >0.113 |
| 24 | H | 8-Cl | H,H | S | C= | —C(=N—CN)—NH—CH$_2$—(pyridyl N-oxide) | 0.038 |
| 27 | H | 8-Cl | H,H | SO$_2$ | C= | *4-piperidinyl with N-Boc and acetyl* | >1.2 |
| 28 | H | 8-Cl | H,H | SO$_2$ | C= | *4-piperidinyl-CH$_2$-C(=O)-* | >1.2 |
| 29 | H | 8-Cl | H,H | SO$_2$ | C= | *4-piperidinyl with N-C(=O)NH$_2$ and acetyl* | >1.1 |
| 33 | H | 8-Cl | H,H | S | C= | *4-fluorophenyl-C(CH$_3$)=CH-CN* | >0.42 |

-continued

TABLE OF COMPOUNDS PREPARED AND ACTIVITIES

| Ex. No. | $X^1$ | $X^2$ | $R^1,R^2$ | Y | A | R | $IC_{50}$ ($\mu$m) |
|---|---|---|---|---|---|---|---|
| 30 | H | 8-Cl | $CH_3, CH_3$ | $SO_2$ | C= | pyridine N-oxide ketone | >1.1 |
| 34 | H | 8-Cl | H,H | N—$CH_3$ | N— | pyridine N-oxide ketone | 2.7 |
| 38 | H | 8-Cl | H,H | N—$CH_3$ | N— | piperidine-N-Boc ketone | >3.6 |
| 35 | H | 8-Cl | H,H | N—$CH_3$ | N— | pyridyl ketone | 0.84 |
| 36 | H | 8-Cl | H,H | N—$CH_3$ | N— | —C($SCH_3$)=N—CN | 1.1 |
| 37 | H | 8-Cl | H,H | N—$CH_3$ | N— | —C(=N—CN)—NH—$CH_2$—pyridyl | 0.14 |
| 39 | H | 8-Cl | H,H | N—$CH_3$ | N— | piperidinyl ketone (NH) | >1.3 |

The compounds of this invention inhibit abnormal cellular growth. Without wishing to be bound by theory, we believe that these compounds may function through the inhibition of G-protein function, such as Ras p21, by blocking G-protein isoprenylation, thus making them useful in the treatment of proliferative diseases such as tumor growth and cancer. Without wishing to be bound by theory, we believe that these compounds inhibit Ras farnesyl protein transferase, and thus show antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells or prostate tumor cells. Also, the inhibition of the abnormal growth of cells by the treatment with a compound of Formula I may be by inhibiting Ras farnesyl protein transferase. The inhibition may be of tumor cells wherein the Ras protein is activated as a result of oncogenic mutation in genes other than the ras gene.

Inert, pharmaceutically acceptable carriers used for preparing pharmaceutical compositions from the FPT inhibitors described herein can be either solid or liquid. Solid preparations include powders, tablets, dispersible granules, capsules, cachets and suppositories. The powders and tablets may comprise from about 5 to about 70% active ingredient. Suitable solid carriers are known in the art, e.g., magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, and allowed to cool and thereby solidify.

Liquid preparations include solutions, suspensions and emulsions. As an example may be mentioned water or water-propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The FPT inhibitors described herein may also be deliverable transdermally. The transdermal compositions can take the form of creams, lotions, aerosols and/or emulsions and can be included in a transdermal patch of the matrix or reservoir type as are conventional in the art for this purpose.

Preferably the compounds are administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the FPT inhibitors described herein will be regulated according to the judgment of the attending clinician considering such factors as age, condition and size of the patient as well as severity of the symptoms being treated. A typical recommended dosage regimen is oral administration of from 10 mg to 2000 mg/day, preferably 10 to 1000 mg/day, in two to four divided doses to block tumor growth. The compounds are substantially non-toxic when administered within this dosage range.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain can also be used to help judge effectiveness of treatment. Moreover, the quality of life of the patient can also be used in this way. For example, a patient's improvement in overall performance, as indicated (for example) by less anorexia (a better appetite), less depression, a more positive outlook, and a general improvement in the quality of life and daily living, can all be used to help assess the patient's general condition and the effectiveness of treatment.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

All publications and patent applications cited herein are incorporated by reference to the same extent as if each individual publication or patent application was specifically and individually indicated to be incorporated by reference.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification; and the invention is not to be limited to the specific embodiments that have been presented herein by way of example.

We claim:
1. Compounds of Formula I

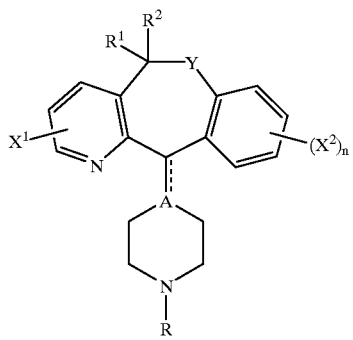

wherein:
$X^2$ is halogen;
n is 1;
$R^1$ and $R^2$ are H;
Y is O, S or $SO_2$;
A is CH and the dotted line indicates a single bond;
R is —CZ—$Y^1$—$Y^2$—$R^3$;
$Y^1$ is $CH_2$;
Z is O; and
  (1) when Y is O then
    (a) $X^1$ is H or halogen;
    (b) $Y^2$ is a bond;
    (c) $R^3$ is selected from: a 3-pyridinyl group 4-pyridinyl group or a 4-pyridinyl-1-oxide group or;
  (2) when Y is S then
    (a) $X^1$ is H;
    (b) $Y^2$ is a bond;
    (c) $R^3$ is selected from: a 4-pyridinyl group or a 4-pyridinyl-1-oxide group, a 1-methyl-4-piperidinyl group, or a 1-$CONH_2$-4-piperidinyl group or;
  (3) when Y is $SO_2$ then
    (a) $X^1$ is H;
    (b) $Y^2$ is a bond;
    (c) $R^3$ is a 4-pyridinyl group; or
  (4) when Y is S then
    (a) $X^1$ is H;
    (b) $Y^2$ is S;
    (c) $R^3$ is a 4-pyridinyl group;
and their pharmaceutically acceptable acid addition salts.

2. The compound of claim 1, namely 4-(3-bromo-8-chloro-5,11-dihydro[1]benzoxepino[4,3-b]-pyridin-11-ylidene)-1-(4-pyridine-acetyl)piperidine N1-oxide having the formula

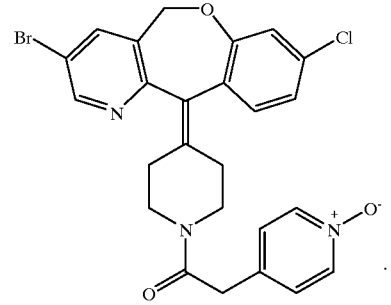

3. The compound of claim 1, namely 4-(8-chloro-5,11-dihydro[1]benzothiepino[4,3-b]pyridin-11-ylidene)-1-(pyridine-4-acetyl)-piperidine having the formula

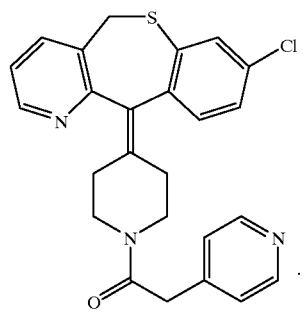

4. The compound of claim 1 selected from the group consisting of:
4-(8-Chloro-5, 11-dihydro[1]benzothiepino[4,3-b]pyridin-11-ylidene)-N-cyano-N'-(4-pyridinylmethyl)-1-piperidine-carboximidamide having the formula

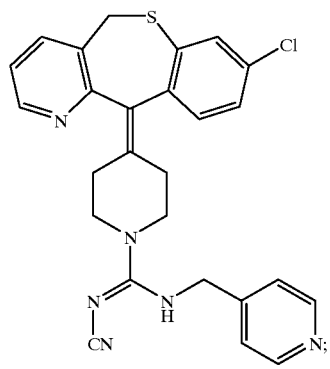

4-(8-chloro-5,11-dihydro[1]benzothiepino[4,3-b]pyridin-11-ylidene)-N-cyano-N'-(3-pyridinylmethyl)-1-piperidine-carboximidamide N1-oxide having the formula

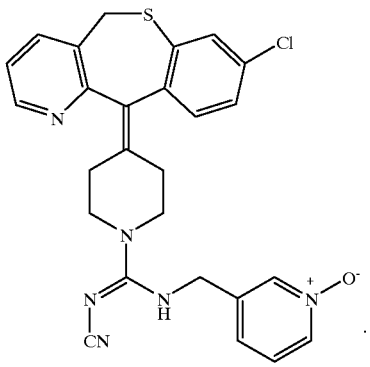

5. Compounds of Formula I

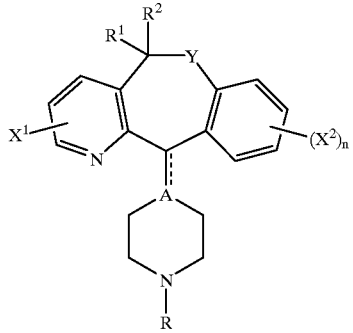

wherein:

$X^1$ is H;

$X^2$ is halogen;

n is 1;

Y is S or O;

$R^1$ and $R^2$ is H;

A is a C atom and the dotted line indicates a double bond;

R is —CZ—$Y^1$—$Y^2$—$R^3$, wherein:

Z is =N—CN;

$Y^1$ is NH;

$Y^2$ is $CH_2$; and (1) when Y is S then $R^3$ is selected from: a 4-pyridinyl group or a 4-pyridinyl-1-oxide group or (2) when Y is O then $R^3$ is a 4-pyridinyl group;

and their pharmaceutically acceptable acid addition salts.

6. The compound of claim 1 wherein $X^1$ is selected hydrogen or Br.

7. The compound of claim 5 wherein $X^2$ is 8-Cl.

8. A compound selected from compounds of the formula:

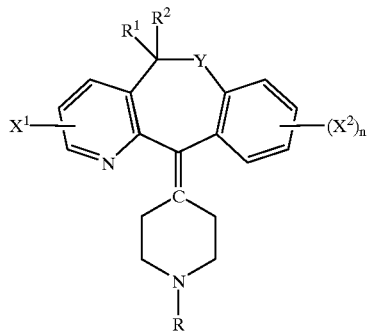

| Ex. No. | $X^1$ | $X^2$ | $R^1$, $R^2$ | Y | R |
|---|---|---|---|---|---|
| 5 | H | 8-Cl | H,H | O | 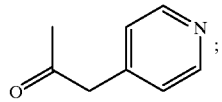 |
| 6 | H | 8-Cl | H,H | O | 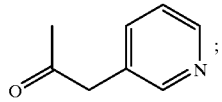 |
| 7B | H | 8-Cl | H,H | O | 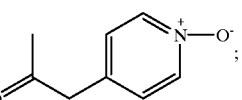 |
| 3 | H | 8-Cl | H,H | O | 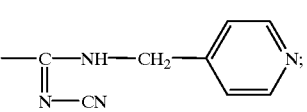 |
| 9B | H | 8-Cl | H,H | S | 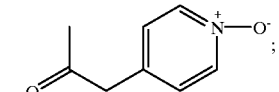 |
| 26 | H | 8-Cl | H,H | S | 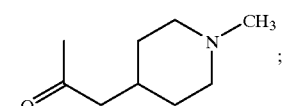 |
| 16B | H | 8-Cl | H,H | $SO_2$ |  |
| 15B | H | 8-Cl | H,H | S |  |
| 14B | H | 8-Cl | H,H | S | 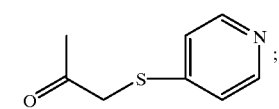 |

-continued

| Ex. No. | X¹ | X² | R¹, R² | Y | R |
|---|---|---|---|---|---|
| 12B | H | 8-Cl | H,H | S | 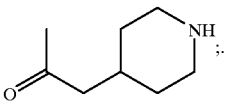 |

9. A compound selected from compounds of the formula:

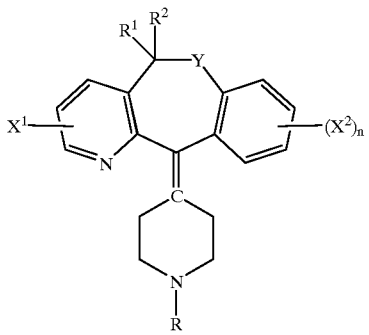

wherein $X^1$, $X^2$, $R^1$, $R^2$, Y and R are:

| Ex. No. | X¹ | X² | R¹, R² | Y | R |
|---|---|---|---|---|---|
| 2 | H | 8-Cl | H,H | O | —C(SCH₃)=N—CN; |
| 11B | H | 8-Cl | H,H | S | 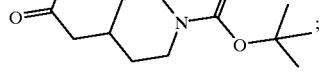 |
| 22 | H | 8-Cl | H,H | S | —C(SCH₃)=N—CN;. |

10. A pharmaceutical composition comprising an effective amount of compound of claim 1 in combination with a pharmaceutically acceptable carrier.

11. A pharmaceutical composition comprising an effective amount of compound of claim 5 in combination with a pharmaceutically acceptable carrier.

* * * * *